United States Patent
Kramer et al.

(10) Patent No.: US 6,936,670 B2
(45) Date of Patent: Aug. 30, 2005

(54) MULTIFUNCTIONAL ALKOXYAMINES BASED ON POLYALKYLPIPERIDINES, POLYALKYLPIPERAZINONES AND POLYALKYLMORPHOLINONES AND THEIR USE AS POLYMERIZATION REGULATORS/INITIATORS

(75) Inventors: Andreas Kramer, Meyriez (CH); Andreas Mühlebach, Frick (CH); Peter Nesvadba, Marly (CH); Marie-Odile Zink, Mulhouse (FR); Tobias Hintermann, Basel (CH)

(73) Assignee: Ciba Specialty Chemical Corp., Tarrytown, NY (US)

( * ) Notice: Subject to any disclaimer, the term of this patent is extended or adjusted under 35 U.S.C. 154(b) by 0 days.

(21) Appl. No.: 10/482,546

(22) PCT Filed: Jun. 27, 2002

(86) PCT No.: PCT/EP02/07131

§ 371 (c)(1), (2), (4) Date: Dec. 30, 2003

(87) PCT Pub. No.: WO03/004471

PCT Pub. Date: Jan. 16, 2003

(65) Prior Publication Data

US 2004/0167303 A1 Aug. 26, 2004

(30) Foreign Application Priority Data

Jul. 5, 2001 (EP) .......................................... 01810664

(51) Int. Cl.$^7$ ............................................. C08F 126/06
(52) U.S. Cl. .................... 526/265; 526/348.7; 526/346; 526/335; 526/264; 526/266; 526/319; 526/341; 526/303.1; 526/343; 526/220; 526/217

(58) Field of Search ............................. 526/265, 348.7, 526/346, 335, 264, 266, 319, 341, 303.1, 343, 220, 217

(56) References Cited

U.S. PATENT DOCUMENTS

| 5,627,248 A | 5/1997 | Koster et al. ............... 526/217 |
| 5,677,388 A | 10/1997 | Koster et al. ............... 525/314 |
| 6,573,347 B1 * | 6/2003 | Wunderlich et al. ..... 526/218.1 |

FOREIGN PATENT DOCUMENTS

| WO | 00/18807 | 4/2000 |
| WO | 00/71501 | 11/2000 |
| WO | 01/02345 | 1/2001 |

OTHER PUBLICATIONS

C. Hawker, Angew. Chem. Int. Ed. Engl. (1995), vol. 34, No. 13/14, pp. 1456–1459.

P. Chaumont et al., Polym. Prep. (1990), vol. 40 (2), pp. 366–367.

* cited by examiner

Primary Examiner—William K. Cheung
(74) Attorney, Agent, or Firm—Tyler A. Stevenson

(57) ABSTRACT

The instant invention relates to multifunctional alkoxyamines based on polyalkylpiperidines, polyalkylpiperazinones and polyalkylmorpholinones and their use as polymerization regulatros/initiators. Further subjects of the invention are a polymerizable composition comprising an ethylenically unsaturated monomer or oligomer and the alkoxyamine compound as well as a process for polymerization and a process for preparation of the compounds.

15 Claims, No Drawings

MULTIFUNCTIONAL ALKOXYAMINES BASED ON POLYALKYLPIPERIDINES, POLYALKYLPIPERAZINONES AND POLYALKYLMORPHOLINONES AND THEIR USE AS POLYMERIZATION REGULATORS/INITIATORS

The instant invention relates to multifunctional alkoxyamines based on polyalkylpiperidines, polyalkylpiperazinones and polyalkylmorpholinones and their use as polymerization regulators/initiators. Further subjects of the invention are a polymerizable composition comprising an ethylenically unsaturated monomer or oligomer and the alkoxyamine compound as well as a process for polymerization and a process for preparation of the compounds.

The initiators/regulators, the polymerization processes and resin products of the present invention are useful in many applications, including a variety of specialty applications, such as for the preparation of block copolymers which are useful as compatibilizing agents for polymer blends, or dispersing agents for coating systems or for the preparation of narrow molecular weight resins or oligomers for use in coating technologies and thermoplastic films or as toner resins and liquid immersion development ink resins or ink additives used for electrophotographic imaging processes.

The concept of having multifunctional alkoxyamines as initiators/regulators for radical polymerization is known. WO 00/71501 for example discloses multifunctional open chain alkoxyamines having a phosphor atom attached to the carbon atom in α-position to the nitrogen atom. The compounds are useful initiators/regulators, however, they are thermally not very stable and can only be used at a polymerization temperature of around 120° C. Limited storage stability is a further drawback of these compounds.

U.S. Pat. Nos. 5,627,248 and 5,677,388 disclose difunctional alkoxyamines on the basis of tetramethylpiperidine. These compounds are not very reactive and only the polymerization of styrene proceeds with reasonable efficiency at high temperatures. Conversion and polymerization rate of acrylates is very low.

WO 00/18807 discloses polymeric macroinitiators which have been prepared by ATRP polymerization wherein the halogen atoms have been replaced by nitroxylether end groups.

WO 01/02345 discloses also multifunctional alkoxyamines. These compounds are all characterized by having a phenyl group attached to the carbon atom in α-position to the oxygen atom of the alkoxyamine group. This aromatic group can have drawbacks in the end use of the polymers. Typically photo stability decreases, when aromatic moieties are present. This leads in many cases to discoloration which is undesirable for many end uses.

Surprisingly, it has now been found that the present compounds are very suitable to prepare (co)polymers particularly block, star, comb (co)polymers and the like, without having the drawbacks of the prior art compounds.

By their multiple alkoxyamine functionality they provide an ideal tool for tailor made polymerization processes. The degree of branches can be chosen by selecting two, three, four or even more alkoxyamine functionalities.

Furthermore with the present invention there are provided initiators/regulators which allow very efficiently to bring into the macromer functional end-groups which come from the initiating radical. The compounds of the present invention thus allow to produce macromers or polymers with a wide variety of functional groups, which was not easily possible until now.

The functionalized macromers or polymers may then be further reacted with suitable modifying compounds to further adjust the polymer's properties.

Polymerization of the monomers results in a polymer or copolymer of narrow polydispersity, higher molecular weight and a high monomer to polymer conversion even at relatively low temperatures and at short reaction times, making the polymerization process particularly suitable for industrial applications. The resulting (co)polymers are of high purity and in many cases colorless, therefore not requiring any further purification. The polymers prepared with the instant compounds show high photo and thermal stability and exhibit only a minor discoloration upon exposure to UV light and heat due to the higher alkoxyamine content.

One subject of the invention is a compound of formula Ia, Ib, Ic or Id

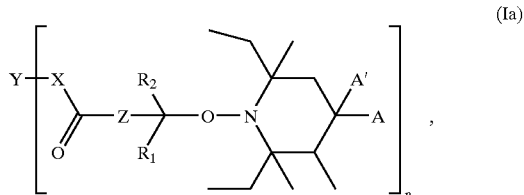

(Ia)

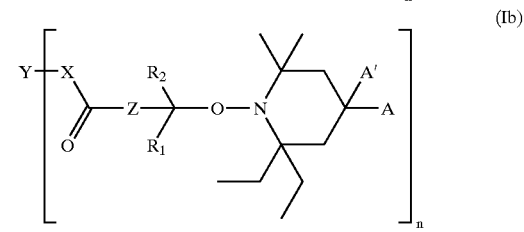

(Ib)

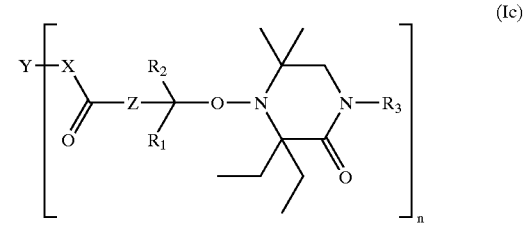

(Ic)

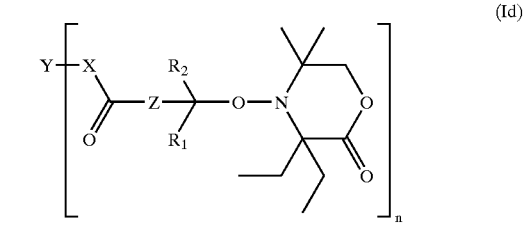

(Id)

wherein
$R_1$ and $R_2$ are independently of each other hydrogen, $C_1$–$C_{18}$alkyl or phenyl;
$R_3$ is hydrogen, $C_1$–$C_{18}$alkyl, $C_1$–$C_{18}$alkyl which is substituted by OH, or phenyl which is unsubstituted or substituted by OH, halogen, $C_1$–$C_8$alkoxy or $C_1$–$C_8$alkyl;
X is O, S, $NR_4$ or, if Z is —O—$CH_2$—, X is additionally a direct bond;
$R_4$ is hydrogen or $C_1$–$C_{18}$alkyl;
Z is a direct bond and if $R_1$ is hydrogen and $R_2$ phenyl, Z is additionally —O—$CH_2$—;
Y is a radical derived from a polyol, a polyamine, a polyaminoalcohol, a polyaminothiol, a polyhydroxythiol, a polyaminohydroxythiol or a polythiol having 2 to 20 —OH, SH and/or —$NR_5$H groups, wherein $R_5$ is hydrogen, $C_1$–$C_{18}$alkyl or phenyl;

or if X is a direct bond and Z is —O—CH$_2$—, Y is a radical derived from a polycarboxylic acid having 2–20 carboxylic functions;

A and A' together are =O; or

A' is hydrogen; and

A is hydrogen, —O—R$_{100}$, wherein R$_{100}$ is hydrogen, C$_1$–C$_{18}$alkyl which is uninterrupted or interrupted by one or more oxygen atoms, NHR$_{100}$, NR$_{100}$R$_{103}$ or cyanoethyl;

or a group

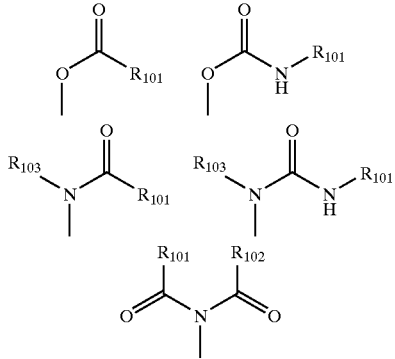

R$_{101}$ is hydrogen, —COOH, —COO(C$_1$–C$_4$alkyl), —COO-phenyl, —COObenzyl, C$_1$–C$_8$alkoxy, C$_1$–C$_{18}$alkyl, C$_2$–C$_4$alkenyl, C$_1$–C$_{18}$alkyl or C$_2$–C$_4$alkenyl substituted by OH, —COOH, —COO(C$_1$–C$_4$)alkyl, C$_2$–C$_{18}$alkyl which may be interrupted by one or more oxygen atom, unsubstituted cyclopentyl, cyclohexyl, cyclohexenyl, phenyl or naphthyl; or cyclopentyl, cyclohexyl, cylohexenyl, phenyl or naphthyl which are substituted by C$_1$–C$_4$alkyl, —COOH or —COO—(C$_1$–C$_4$alkyl)

R$_{102}$ is hydrogen, C$_1$–C$_{18}$alkyl or R$_{101}$ and R$_{102}$ together with the nitrogen atom form a 5-membered ring which may have an unsaturated bond or be fused to a benzene ring;

R$_{103}$ is hydrogen or C$_1$–C$_{18}$alky; or

A and A' together are a group

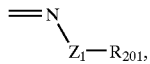

wherein

Z$_1$ is O, NR$_{202}$ or when R$_{201}$, represents alkyl or aryl Z$_1$ is additionally a direct bond;

R$_{202}$ is H, C$_1$–C$_{18}$alkyl or phenyl;

R$_{201}$ is H, straight or branched C$_1$–C$_{18}$alkyl or C$_3$–C$_{18}$alkenyl, which may be unsubstituted or substitued, by one or more OH, C$_1$–C$_8$alkoxy, carboxy, C$_1$–C$_8$alkoxycarbonyl, C$_5$–C$_{12}$cycloalkyl or C$_5$–C$_{12}$cycloalkenyl;

phenyl, C$_7$–C$_9$phenylalkyl or naphthyl which may be unsubstituted or substituted by one or more C$_1$–C$_8$alkyl, halogen, OH, C$_1$–C$_8$alkoxy, carboxy, C$_1$–C$_8$alkoxycarbonyl; or —C(O)—C$_1$–C$_{18}$alkyl, or an acyl moiety of a α,β-unsaturated carboxylic acid having 3 to 9 carbon atoms or of an aromatic carboxylic acid having 7 to 15 carbon atoms;

—SO$_3$$^-$Me$^+$, —PO(O$^-$Me$^+$)$_2$, —P(O)(OR$_2$)$_2$, —SO$_2$R$_2$, —CO—NH—R$_2$, —CONH$_2$, COOR$_2$, or Si(Me)$_3$, wherein Me$^+$ is =H$^+$, ammonium or an alkali metal cation; or A is O—Y$_1$ and A' is O—Y$_2$ forming a ketale structure in the 4 position; wherein Y$_1$ and Y$_2$ are independently C$_1$–C$_{12}$alkyl, C$_3$–C$_{12}$alkenyl, C$_3$–C$_{12}$alkinyl, C$_5$–C$_8$cycloalkyl, phenyl, naphthyl, C$_7$–C$_9$phenylalkyl; or Y$_1$ and Y$_2$ together form one of the bivalent groups —C(R$_{301}$)(R$_{302}$)—CH(R$_{303}$)—, —CH(R$_{301}$)—CH$_2$—C(R$_{302}$)(R$_{303}$)—, —CH(R$_{302}$)—CH$_2$—C(R$_{301}$)(R$_{303}$)—, —CH$_2$—C(R$_{301}$)(R$_{302}$)—CH(R$_{303}$)—, o-phenylene, 1,2-cyclohexyliden, —CH$_2$—CH=CH—CH$_2$— or

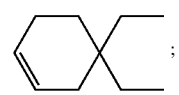

wherein

R$_{301}$ is hydrogen, C$_1$–C$_{12}$alkyl, COOH, COO—(C$_1$–C$_{12}$)alkyl or CH$_2$OR$_{304}$;

R$_{302}$ and R$_{303}$ are independently hydrogen, methyl, ethyl, COOH or COO—(C$_1$–C$_{12}$)alkyl;

R$_{304}$ is hydrogen, C$_1$–C$_{12}$alkyl, benzyl, or a monovalent acyl residue derived from an aliphatic, cycloaliphatic or aromatic monocarboxylic acid having up to 18 carbon atoms.

Halogen is F, Cl, Br, I, preferably Cl or Br.

C$_1$–C$_{18}$alkyl can be linear or branched. Examples are methyl, ethyl, propyl, isopropyl, butyl, 2-butyl, isobutyl, t-butyl, pentyl, 2-pentyl, hexyl, heptyl, octyl, 2-ethylhexyl, t-octyl, nonyl, decyl, undecyl or dodecyl.

C$_2$–C$_{18}$alkyl interrupted by at least one O atom is for example —CH$_2$—CH$_2$—O—CH$_2$—CH$_3$, —CH$_2$—CH$_2$—O—CH$_3$ or —CH$_2$—CH$_2$—O—CH$_2$—CH$_2$—O—CH$_2$—CH$_3$. It is preferably derived from polyethylene glycol. A general description is —((CH$_2$)$_a$—O)$_b$—H/CH$_3$, wherein a is a number from 1 to 6 and b is a number from 2 to 10.

Further examples of C$_2$–C$_{18}$alkyl interrupted by —O— are for example 3-oxapentane, 4-oxaheptane, 3,6-dioxaoctane, 4,7-dioxadecane, 4,9-dioxadodecane, 3,6,9-trioxaundecane and 4,7,10-trioxatridecane.

Alkyl substituted by a group —COOH is for example CH$_2$—COOH, CH$_2$—CH$_2$—COOH, (CH$_2$)$_3$—COOH or CH$_2$—CHCOOH—CH$_2$—CH$_3$ Hydroxyl- or alkoxycarbonyl substituted C$_1$–C$_{18}$alkyl can be, for example, 2-hydroxyethyl, 2-hydroxypropyl, methoxycarbonylmethyl or 2-ethoxycarbonylethyl, 2-hydroxyethyl is preferred.

Alkenyl having from 3 to 18 carbon atoms is a branched or unbranched radical, for example propenyl, 2-butenyl, 3-butenyl, isobutenyl, n-2,4-pentadienyl, 3-methyl-2-butenyl, n-2-octenyl, n-2-dodecenyl, isododecenyl.

Examples of alkoxy are methoxy, ethoxy, propoxy, isopropoxy, butoxy, isobutoxy, pentoxy, isopentoxy, hexoxy, heptoxy or octoxy.

Aryl is phenyl or naphthyl.

C$_7$–C$_9$phenylalkyl is for example benzyl, α-methylbenzyl, α,α-dimethylbenzyl or 2-phenylethyl, benzyl is preferred.

C$_5$–C$_{12}$cycloalkyl is for example cyclopentyl, cyclohexyl, cycloheptyl, methylcyclopentyl or cyclooctyl.

C$_5$–C$_{12}$cycloalkenyl is for example 3-cyclopentenyl, 3-cyclohexenyl or 3-cycloheptenyl.

If R$_1$ is a monovalent radical of a α, β-unsaturated or aromatic carboxylic acid, it is, for example, an acryloyl, methacryloyl, benzoyl or β-(3,5di-tert-butyl-4-hydroxyphenyl)propionyl radical.

A monovalent radical of an aliphatic carboxylic acid is for example acetyl, propionyl, butyryl, caproyl, stearoyl or oleyl.

Preferred is a compound of formula Ia, Ib, Ic or Id wherein
X is O or $NR_4$, wherein $R_4$ is hydrogen or $C_1$–$C_8$alkyl;
Z is a direct bond;
$R_1$ is hydrogen or $C_1$–$C_{18}$alkyl; and
$R_2$ is $C_1$–$C_{18}$alkyl and the other substituents are as defined above.

More preferred is a compound of formula Ia, Ib, Ic or Id wherein
A and A' together are =O; or
A' is hydrogen and
A is hydrogen, OH, $OR_{100}$, $NHR_{100}$, $NR_{100}R_{103}$ or a group

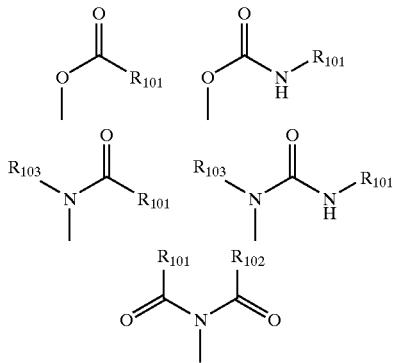

wherein $R_{100}$, $R_{101}$, $R_{102}$ and $R_{103}$ independently are hydrogen or $C_1$–$C_{18}$alkyl; or
A is O—$Y_1$ and A' is O—$Y_2$ forming a ketale structure in the 4 position; wherein
$Y_1$ and $Y_2$ are independently $C_1$–$C_{12}$alkyl, phenyl or benzyl; or
$Y_1$ and $Y_2$ together form one of the bivalent groups —C($R_{301}$)($R_{302}$)—CH($R_{303}$)—, CH($R_{301}$)—$CH_2$—C($R_{302}$)($R_{303}$)—, —CH($R_{302}$)—$CH_2$—C($R_{301}$)($R_{303}$)—, —$CH_2$—C($R_{301}$)($R_{302}$)—CH($R_{303}$)—, or —$CH_2$—CH=CH—$CH_2$—, wherein
$R_{301}$ is hydrogen, $C_1$–$C_{12}$alkyl or COO—($C_1$–$C_{12}$)alkyl; and
$R_{302}$ and $R_{303}$ are independently hydrogen, methyl ethyl or COO—($C_1$–$C_{12}$)alkyl.

Y is an organic radical derived from a polyfunctional alcohol, polyfunctional aminoalcohol, polyfunctional amine, polyfunctional mercaptane, polyfunctional phenol or polyfunctional thiophenol.

The polyfunctional alcohol can be an aliphatic polyfunctional alcohol, a cycloaliphatic polyol or an aromatic polyol.

The aliphatic polyfunctional alcohol can contain 2 to 20 carbon atoms, the cycloaliphatic polyols 5 to 12 carbon atoms and the aromatic polyols 6 to 18 carbon atoms.

Polyoxyalkylene glycols having a molecular weight from 150 to 40000 can also be used.

Aromatic polyols are those, wherein at least two hydroxyl groups are bound to one or to different aromatic hydrocarboxylic radicals.

Suitable aliphatic polyols are for example diols which are linear or branched aliphatic glycols, in particular those containing 2 to 12, preferably 2 to 6, carbon atoms in the molecule, for example: ethylene glycol, 1,2- and 1,3-propylene glycol, 1,2-, 1,3-, 2,3- or 1,4-butanediol, pentyl glycol, neopentyl glycol, 1,6-hexanediol, 1,12-dodecanediol. A suitable cycloaliphatic diol is, for example, 1,4-dihydroxycyclohexane. Other suitable aliphatic diols are, for example, 1,4-bis(hydroxymethyl)cyclohexane, aromatic-aliphatic diols, such as p-xylylene glycol or 2,5-dichloro-p-xylylene glycol, 2,2-(β-hydroxyethoxyphenyl) propane and polyoxyalkylene glycols, such as diethylene glycol, triethylene glycol, polyethylene glycol or polypropylene glycol. The alkylenediols are preferably linear and preferably contain 2 to 4 carbon atoms.

Other suitable diols are the β-hydroxyalkylated, in particular β-hydroxyethylated bisphenols, such as 2,2-bis[4'-(β-hydroxyethoxy)phenyl]propane.

Another group of suitable aliphatic diols are the heterocyclic diols described in the German published patent specifications 1812003, 2342432, 2342372 and 2453326. Examples are: N,N'-bis(β-hydroxyethyl)-5,5-dimethylhydantoin, N,N'-bis(β-hydroxypropyl)-5,5-dimethylhydantoin, methylenebis-[N-(β-hydroxyethyl)-5-methyl-5-ethylhydantoin], methylenebis-[N-(β-hydroxyethyl)-5,5-dimethylhydantoin], N,N'-bis(β-hydroxyethyl)benzimidazolone, N,N'-bis(β-hydroxyethyl)-(tetrachloro)benzimidazolone or N,N'-bis(β-hydroxyethyl)-(tetrabromo)benzimidazolone.

Suitable aromatic diols are mononuclear diphenols and, in particular, dinuclear diphenols carrying a hydroxyl group at each aromatic nucleus. The term aromatic will be taken to mean preferably hydrocarbonaromatic radicals such as phenylene or naphthylene. Besides e.g. hydroquinone, resorcinol or 1,5-, 2,6- and 2,7-dihydroxynaphthalene, 9,10-dihydroxyanthracene, 4,4'-dihydroxybiphenyl, bisphenols merit particular mention.

Examples of bisphenols are: bis(p-hydroxyphenyl) ether or bis(p-hydroxyphenyl) thioether, bis(p-hydroxyphenyl) sulfone, bis(p-hydroxyphenyl)methane, bis(4-hydroxyphenyl)-2,2'-biphenyl, phenylhydroquinone, 1,2-bis (p-hydroxyphenyl)ethane, 1-phenyl-bis(p-hydroxyphenyl) methane, diphenyl-bis(p-hydroxyphenyl)methane, diphenyl-bis(p-hydroxyphenyl)ethane, bis(3,5-dimethyl-4-hydroxyphenyl)sulfone, bis(3,5-dimethyl-4-hydroxyphenyl)-p-diisopropylbenzene, bis(3,5-dimethyl-4-hydroxyphenyl)-m-diisopropylbenzene, 2,2-bis(3',5'-dimethyl-4'-hydroxyphenyl)propane, 1,1- or 2,2-bis(p-hydroxyphenyl)butane, 2,2-bis(p-hydroxyphenyl) hexafluoropropane, 1,1-dichloro- or 1,1,1-trichloro-2,2-bis (p-hydroxyphenyl)ethane, 1,1-bis(p-hydroxyphenyl) cyclopentane and, in particular, 2,2-bis(p-hydroxyphenyl) propane (bisphenol-A) and 1,1-bis(p-hydroxyphenyl) cyclohexane (bisphenol-C).

A suitable triol is for example

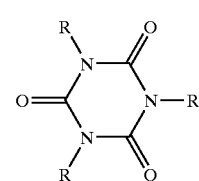

R=$CH_2$—$CH_2$—OH.

Other suitable aliphatic triols are for example glycerin or trimethylolpropane.

Examples for a tetrafunctional alcohol are erythritol, threitol or pentaerythritol.

Higher alcohols are for example pentahydroles, for example xylitol or arabitol and hexahydrols, for example sorbitol, mannitol, dulcitol, talitol, iditol, inositol.

In principal all hydroxylated aliphatic hydrocarbon compounds are suitable as multifunctional alcohols.

The polyaminoalcohols or polyamines can be deduced from the above mentioned polyalcohols by replacing one or more hydroxyl groups by amino groups.

Primary amino groups are preferred, which may be attached to aromatic rings or alkyl groups as mentioned above for the corresponding alcohols.

Suitable mercaptanes or thiophenols are those which are derived by substituting the oxygen atom by a sulfur atom in the above mentioned examples.

If X is a direct bond and Z is —O—CH$_2$—, then Y is a radical derived from a polycarboxylic acid having 2–20 carboxylic functions.

Suitable polycarboxylic acids are for example dicarboxylic acids like oxalic acid, malonic acid, succinic acid, fumaric acid, glutaric acid, adipic acid, 1,12-dodecandioic acid, phthalic-, isophthalic- or terephthalic acid, isomeric naphthalene dicarboxylic acids, tricarboxylic acids like citric acid, nitrilotriacetic acid or 1,2,4-benzentricarboxylic acid, tetracarboxylic acids like ethylenediamine tetraacetic acid or pyromellitic acid, pentacarboxylic acids like for example diethylenetriaminepentaacetic acid, hexacarboxylic acids like for example mellitic acid or triethylenetetraminehexaacetic acid.

Preferably Y is a radical derived from a polyol or polyamine, having 2 to 20 —OH or —NR$_5$H groups, wherein R$_5$ is hydrogen, C$_1$–C$_{18}$alkyl or phenyl.

More preferably Y is an aliphatic polyol. Examples have been already mentioned.

Preferably n is a number from 2–20, more preferably from 2–10 and most preferably from 2–6.

Most preferred is a compound of formula Ia or Ib, to which the preferences given above may also apply.

Particularly suitable compounds are

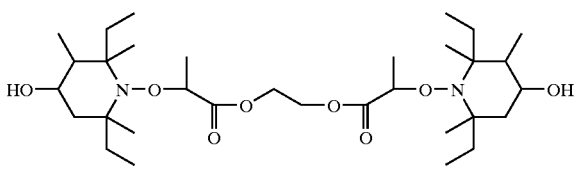

compound 101 of Table 1,

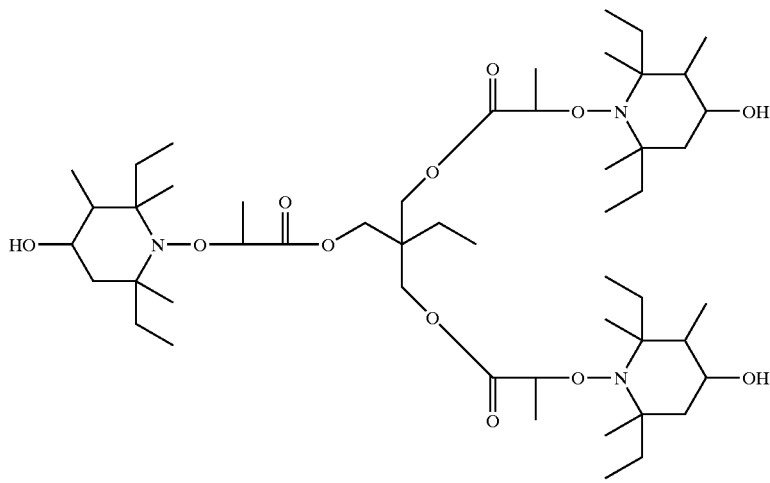

compound 107 of Table 1,

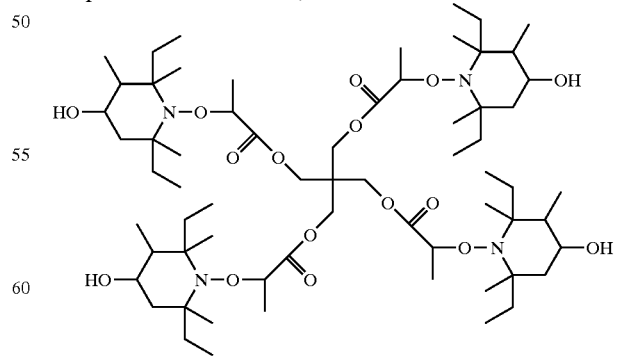

compound 109 of Table 1 and

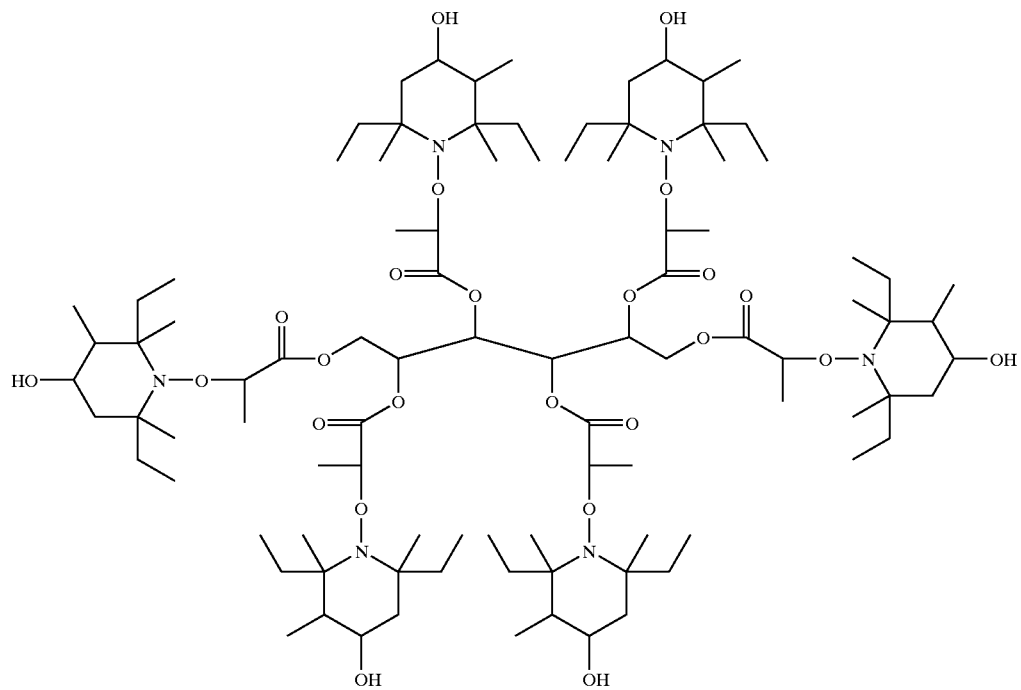

compound 110 of Table 1.

A further subject of the invention is a polymerizable composition, comprising a) at least one ethylenically unsaturated monomer or oligomer, and b) a compound of formula Ia, Ib, Ic or Id or a mixture thereof

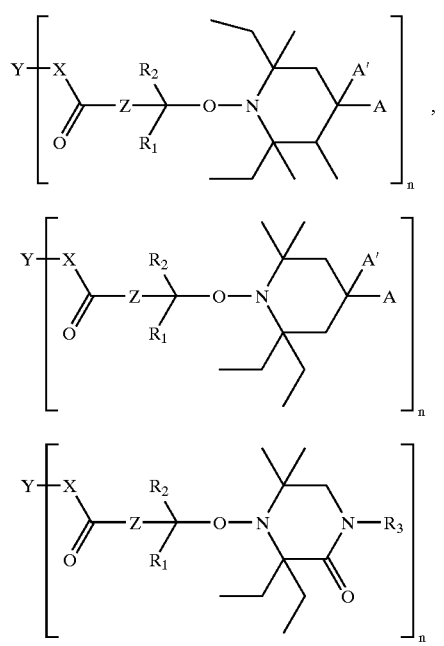

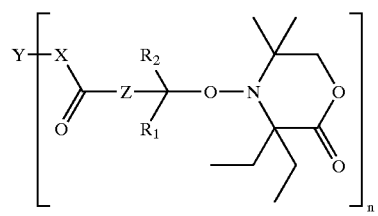

wherein $R_1$ and $R_2$ are independently of each other hydrogen, $C_1$–$C_{18}$alkyl or phenyl;

$R_3$ is hydrogen, $C_1$–$C_{18}$alkyl, $C_1$–$C_{18}$alkyl which is substituted by OH, or phenyl which is unsubstituted or substituted by OH, halogen, $C_1$–$C_8$alkoxy or $C_1$–$C_8$alkyl;

X is O, S, $NR_4$ or, if Z is —O—$CH_2$—, X is additionally a direct bond;

$R_4$ is hydrogen or $C_1$–$C_{18}$alkyl;

Z is a direct bond and if $R_1$ is hydrogen and $R_2$ phenyl, Z is additionally —O—$CH_2$—;

Y is a radical derived from a polyol, a polyamine, a polyaminoalcohol, a polyaminothiol, a polyhydroxythiol, a polyaminohydroxythiol or a polythiol having 2 to 20 —OH, SH and/or —$NR_5$H groups, wherein $R_5$ is hydrogen, $C_1$–$C_{18}$alkyl or phenyl;

or if X is a direct bond and Z is —O—$CH_2$—, Y is a radical derived from a polycarboxylic acid having 2–20 carboxylic functions;

A and A' together are =O; or

A' is hydrogen; and

A is hydrogen, —O—$R_{100}$, wherein $R_{100}$ is hydrogen, $C_1$–$C_{18}$alkyl which is uninterrupted or interrupted by one or more oxygen atoms, $NHR_{100}$, $NR_{100}R_{103}$ or cyanoethyl; or a group

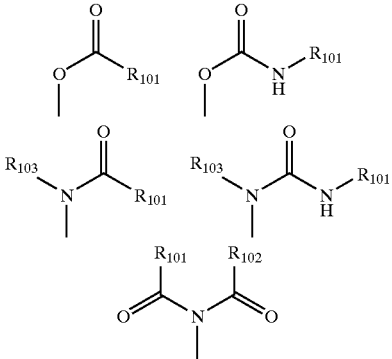

$R_{101}$ is hydrogen, —COOH, —COO($C_1$–$C_4$alkyl), —COO-phenyl, —COObenzyl, $C_1$–$C_8$alkoxy, $C_1$–$C_{18}$alkyl, $C_2$–$C_4$alkenyl, $C_1$–$C_{18}$alkyl or $C_2$–$C_4$alkenyl substituted by OH, —COOH, —COO($C_1$–$C_4$)alkyl, $C_2$–$C_{18}$alkyl which may be interrupted by one or more oxygen atom, unsubstituted cyclopentyl, cyclohexyl, cyclohexenyl, phenyl or naphthyl; or cyclopentyl, cyclohexyl, cylohexenyl, phenyl or naphthyl which are substituted by $C_1$–$C_4$alkyl, —COOH or —COO—($C_1$–$C_4$alkyl)

$R_{102}$ is hydrogen, $C_1$–$C_{18}$alkyl or $R_{101}$, and $R_{102}$ together with the nitrogen atom form a 5-membered ring which may have an unsaturated bond or be fused to a benzene ring;

$R_{103}$ is hydrogen or $C_1$–$C_{18}$alkyl; or

A and A' together are a group

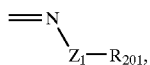

wherein $Z_1$ is O, $NR_{202}$ or when $R_{201}$ represents alkyl or aryl $Z_1$ is additionally a direct bond;

$R_{202}$ is H, $C_1$–$C_{18}$alkyl or phenyl;

$R_{201}$ is H, straight or branched $C_1$–$C_{18}$alkyl or $C_3$–$C_{18}$alkenyl, which may be unsubstituted or substitued, by one or more OH, $C_1$–$C_8$alkoxy, carboxy, $C_1$–$C_8$alkoxycarbonyl, $C_5$–$C_{12}$cycloalkyl or $C_5$–$C_{12}$cycloalkenyl;

phenyl, $C_7$–$C_9$phenylalkyl or naphthyl which may be unsubstituted or substituted by one or more $C_1$–$C_8$alkyl, halogen, OH, $C_1$–$C_8$alkoxy, carboxy, $C_1$–$C_8$alkoxycarbonyl; or —C(O)—$C_1$–$C_{18}$alkyl, or an acyl moiety of a α,β-unsaturated carboxylic acid having 3 to 9 carbon atoms or of an aromatic carboxylic acid having 7 to 15 carbon atoms;

—$SO_3^-Me^+$, —PO($O^-Me^+$)$_2$, —P(O)($OR_2$)$_2$, —$SO_2R_2$, —CO—NH—$R_2$, —$CONH_2$, $COOR_2$, or $Si(Me)_3$, wherein $Me^+$ is $=H^+$, ammonium or an alkali metal cation; or A is O—$Y$, and A' is O—$Y_2$ forming a ketale structure in the 4 position; wherein $Y_1$ and $Y_2$ are independently $C_1$–$C_{12}$alkyl, $C_3$–$C_{12}$alkenyl, $C_3$–$C_{12}$alkinyl, $C_5$–$C_8$cycloalkyl, phenyl, naphthyl, $C_7$–$C_9$phenylalkyl; or $Y_1$ and $Y_2$ together form one of the bivalent groups —C($R_{301}$)($R_{302}$)—CH($R_{303}$)—, —CH($R_{301}$)—$CH_2$—C($R_{302}$)($R_{303}$)—, —CH($R_{302}$)—$CH_2$—C($R_{301}$)($R_{303}$)—,
—$CH_2$C($R_{301}$)($R_{302}$)—CH($R_{303}$)—, o-phenylene, 1,2-cyclohexyliden,
—$CH_2$—CH=CH—$CH_2$— or

wherein $R_{301}$ is hydrogen, $C_1$–$C_{12}$alkyl, COOH, COO—($C_1$–$C_{12}$)alkyl or $CH_2OR_{304}$;

$R_{302}$ and $R_{303}$ are independently hydrogen, methyl, ethyl, COOH or COO—($C_1$–$C_{12}$)alkyl;

$R_{304}$ is hydrogen, $C_1$–$C_{12}$alkyl, benzyl, or a monovalent acyl residue derived from an aliphatic, cycloaliphatic or aromatic monocarboxylic acid having up to 18 carbon atoms.

Definitions and preferences for the individual substituents have been mentioned above.

Preferably the initiator/regulator compound of formula (Ia), (Ib), (Ic) or (Id) is present in an amount of from 0.01 mol-% to 20 mol-% more preferably in an amount of from 0.01 mol-% to 10 mol-% and most preferred in an amount of from 0.05 mol-% to 10 mol-% based on the monomer or monomer mixture.

It is also possible to use a mixture of different initiators/regulators.

When monomer mixtures are used mol-% is calculated on the average molecular weight of the mixture.

Preferably the ethylenically unsaturated monomer or oligomer is selected from the group consisting of ethylene, propylene, n-butylene, n-butylene, styrene, substituted styrene, conjugated dienes, acrolein, vinyl acetate, vinylpyrrolidone, vinylimidazole, maleic anhydride, (alkyl) acrylic acidanhydrides, (alkyl)acrylic acid salts, (alkyl) acrylic esters, (meth)acrylonitriles, (alkyl)acrylamides, vinyl halides or vinylidene halides.

Particularly the ethylenically unsaturated monomers are ethylene, propylene, n-butylene, i-butylene, isoprene, 1,3-butadiene, α-$C_5$–$C_{18}$alkene, styrene, α-methyl styrene, p-methyl styrene or a compound of formula $CH_2$=C($R_a$)—(C=Z)—$R_b$, wherein $R_a$ is hydrogen or $C_1$–$C_4$alkyl, $R_b$ is $NH_2$, $O^-(Me^+)$, glycidyl, unsubstituted $C_1$–$C_{18}$alkoxy, $C_2$–$C_{100}$alkoxy interrupted by at least one N and/or O atom, or hydroxy-substituted $C_1$–$C_{18}$alkoxy, unsubstituted $C_1$–$C_{18}$alkylamino, di($C_1$–$C_{18}$alkyl)amino, hydroxy-substituted $C_1$–$C_{18}$alkylamino or hydroxy-substituted di($C_1$–$C_{18}$alkyl)amino, —O—$CH_2$—$CH_2$—N($CH_3$)$_2$ or —O—$CH_2$—$CH_2$—$N^+H(CH_3)_2$ $An^-$;

$An^-$ is a anion of a monovalent organic or inorganic acid;

Me is a monovalent metal atom or the ammonium ion.

Z is oxygen or sulfur.

Examples for $R_a$ as $C_2$–$C_{100}$alkoxy interrupted by at least one O atom are of formula

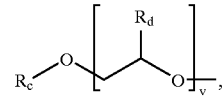

wherein $R_c$ is $C_1$–$C_{25}$alkyl, phenyl or phenyl substituted by $C_1$–$C_{18}$alkyl, $R_d$ is hydrogen or methyl and v is a number from 1 to 50. These monomers are for example derived from non ionic surfactants by acrylation of the corresponding alkoxylated alcohols or phenols. The repeating units may be derived from ethylene oxide, propylene oxide or mixtures of both.

Further examples of suitable acrylate or methacrylate monomers are given below.

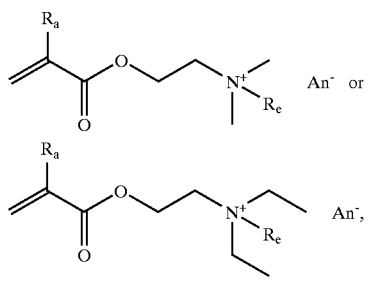

wherein An⁻ and $R_a$ have the meaning as defined above and $R_e$ is methyl or benzyl. An⁻ is preferably Cl⁻, Br⁻ or ⁻O₃S—CH₃.

Further acrylate monomers are

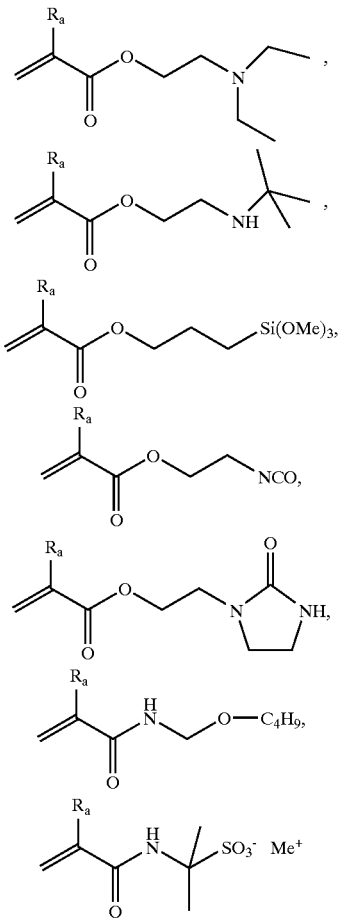

Examples for suitable monomers other than acrylates are

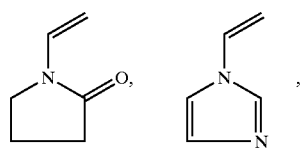

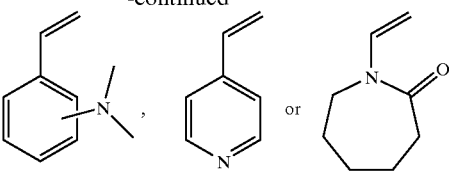

Preferably $R_a$ is hydrogen or methyl, $R_b$ is NH₂, gycidyl, unsubstituted or with hydroxy substituted $C_1$–$C_4$alkoxy, unsubstituted $C_1$–$C_4$alkylamino, di($C_1$–$C_4$alkyl)amino, hydroxy-substituted $C_1$–$C_4$alkylamino or hydroxy-substituted di($C_1$–$C_4$alkyl)amino; and Z is oxygen.

Particularly preferred ethylenically unsaturated monomers are styrene, methylacrylate, ethylacrylate, butylacrylate, isobutylacrylate, tert. butylacrylate, hydroxyethylacrylate, hydroxypropylacrylate, dimethylaminoethylacrylate, glycidylacrylates, methyl (meth)acrylate, ethyl(meth)acrylate, butyl(meth)acrylate, hydroxyethyl(meth)acrylate, hydroxypropyl(meth)acrylate, dimethylaminoethyl(meth)acrylate, glycidyl(meth) acrylates, acrylonitrile, acrylamide, methacrylamide or dimethylaminopropyl-methacrylamide.

A further subject of the invention is a process for preparing an oligomer, a cooligomer, a polymer or a copolymer (block or random) by free radical polymerization of at least one ethylenically unsaturated monomer or oligomer, which comprises (co)polymerizing the monomer or monomers/oligomers in the presence of an initiator compound of formula (Ia), (Ib), (Ic) or (Id) under reaction conditions capable of effecting scission of the O—C bond to form two free radicals, the radical

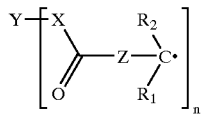

being capable of initiating polymerization.

Preferred is a process wherein the scission of the O—C bond is effected by ultrasonic treatment, heating or exposure to electromagnetic radiation, ranging from γ to microwaves.

More preferably the scission of the O—C bond is effected by heating and takes place at a temperature of between 50° C. and 160° C.

The process may be carried out in the presence of an organic solvent or in the presence of water or in mixtures of organic solvents and water. Additional cosolvents or surfactants, such as glycols or ammonium salts of fatty acids, may be present. Other suitable cosolvents are described hereinafter.

Preferred processes use as little solvents as possible. In the reaction mixture it is preferred to use more than 30% by weight of monomer and initiator, particularly preferably more than 50% and most preferrably more than 80%.

If organic solvents are used, suitable solvents or mixtures of solvents are typically pure alkanes (hexane, heptane, octane, isooctane), hydrocarbons (benzene, toluene, xylene), halogenated hydrocarbons (chlorobenzene), alkanols (methanol, ethanol, ethylene glycol, ethylene glycol monomethyl ether), esters (ethyl acetate, propyl, butyl or hexyl acetate) and ethers (diethyl ether, dibutyl ether, ethylene glycol dimethyl ether), or mixtures thereof.

The aqueous polymerization reactions can be supplemented with a water-miscible or hydrophilic cosolvent to help ensure that the reaction mixture remains a homogeneous single phase throughout the monomer conversion. Any water-soluble or water-miscible cosolvent may be used, as long as the aqueous solvent medium is effective in providing a solvent system which prevents precipitation or phase separation of the reactants or polymer products until after all polymerization reactions have been completed. Exemplary cosolvents useful in the present invention may be selected from the group consisting of aliphatic alcohols, glycols, ethers, glycol ethers, pyrrolidines, N-alkyl pyrrolidinones, N-alkyl pyrrolidones, polyethylene glycols, polypropylene glycols, amides, carboxylic acids and salts thereof, esters, organosulfides, sulfoxides, sulfones, alcohol derivatives, hydroxyether derivatives such as butyl carbitol or cellosolve, amino alcohols, ketones, and the like, as well as derivatives thereof and mixtures thereof. Specific examples include methanol, ethanol, propanol, dioxane, ethylene glycol, propylene glycol, diethylene glycol, glycerol, dipropylene glycol, tetrahydrofuran, and other water-soluble or water-miscible materials, and mixtures thereof. When mixtures of water and water-soluble or water-miscible organic liquids are selected as the aqueous reaction media, the water to cosolvent weight ratio is typically in the range of about 100:0 to about 10:90.

The process is particularly useful for the preparation of block copolymers.

Block copolymers are, for example, block copolymers of polystyrene and polyacrylate (e.g., poly(styrene-co-acrylate) or poly(styrene-co-acrylate-co-styrene). They are usefull as adhesives or as compatibilizers for polymer blends or as polymer toughening agents. Poly(methylmethacrylate-co-acrylate) diblock copolymers or poly(methylacrylate-co-acrylate-co-methacrylate) triblock copolymers) are useful as dispersing agents for coating systeme, as coating additives (e.g. rheological agents, compatibilizers, reactive diluents) or as resin component in coatings (e.g. high solid paints) Block copolymers of styrene, (meth)acrylates and/or acrylontrile are useful for plastics, elastomers and adhesives.

Furthermore, block copolymers of this invention, wherein the blocks alternate between polar monomers and non-polar monomers, are useful in many applications as amphiphilic surfactants or dispersants for preparing highly uniform polymer blends.

The (co)polymers of the present invention may have a number average molecular weight from 1 000 to 400 000 g/mol, preferably from 2000 to 250 000 g/mol and, more preferably, from 2 000 to 200 000 g/mol. When produced in bulk, the number average molecular weight may be up to 500 000 (with the same minimum weights as mentioned above). The number average molecular weight may be determined by size exclusion chromatography (SEC), gel permeation chromatography (GPC), matrix assisted laser desorption/ionization mass spectrometry (MALDI-MS) or, if the initiator carries a group which can be easily distinguished from the monomer(s), by NMR spectroscopy or other conventional methods.

The polymers or copolymers of the present invention have preferably a polydispersity of from 1.0 to 2, more preferably of from 1.1 to 1.9 and most preferably from 1.1 to 1.8.

Thus, the present invention also encompasses in the synthesis novel block, multi-block, star, gradient, random, hyperbranched and dendritic copolymers, as well as graft or copolymers.

The polymers prepared by the present invention are useful for following applications:
adhesives, detergents, dispersants, emulsifiers, surfactants, defoamers, adhesion promoters, corrosion inhibitors, viscosity improvers, lubricants, rheology modifiers, thickeners, crosslinkers, paper treatment, water treatment, electronic materials, paints, coatings, photography, ink materials, imaging materials, superabsorbants, cosmetics, hair products, preservatives, biocide materials or modifiers for asphalt, leather, textiles, ceramics and wood.

Because the present polymerizaton is a "living" polymerization, it can be started and stopped practically at will. Furthermore, the polymer product retains the functional alkoxyamine group allowing a continuation of the polymerization in a living matter. Thus, in one embodiment of this invention, once the first monomer is consumed in the initial polymerizing step a second monomer can then be added to form a second block on the growing polymer chain in a second polymerization step. Therefore it is possible to carry out additional polymerizations with the same or different monomer(s) to prepare multi-block copolymers.

Furthermore, since this is a radical polymerization, blocks can be prepared in essentially any order. One is not necessarily restricted to preparing block copolymers where the sequential polymerizing steps must flow from the least stabilized polymer intermediate to the most stabilized polymer intermediate, such as is the case in ionic polymerization. Thus it is possible to prepare a multi-block copolymer in which a polyacrylonitrile or a poly(meth)acrylate block is prepared first, then a styrene or butadiene block is attached thereto, and so on.

Furthermore, there is no linking group required for joining the different blocks of the present block copolymer. One can simply add successive monomers to form successive blocks.

A plurality of specifically designed polymers and copolymers are accessible by the present invention, such as star and graft (co)polymers as described, inter alia, by C. J. Hawker in Angew. Chemie, 1995, 107, pages 1623–1627, dendrimers as described by K. Matyaszewski et al. in Macrmolecules 1996, Vol 29, No. 12, pages 4167–4171, graft (co)polymers as described by C. J. Hawker et al. in Macromol. Chem. Phys. 198, 155–166(1997), random copolymers as described by C. J. Hawker in Macromolecules 1996, 29, 2686–2688, or diblock and triblock copolymers as described by N. A. Listigovers in Macromolecules 1996, 29, 8992–8993.

A further subject of the invention is the use of a compound of formula Ia, Ib, Ic or Id for the controlled radical (co) polymerization of ethylenically unsaturated monomers.

The compounds of formula Ia, Ib, Ic and Id are prepared according to the following reaction scheme which is illustrative for a compound of formula Ia:

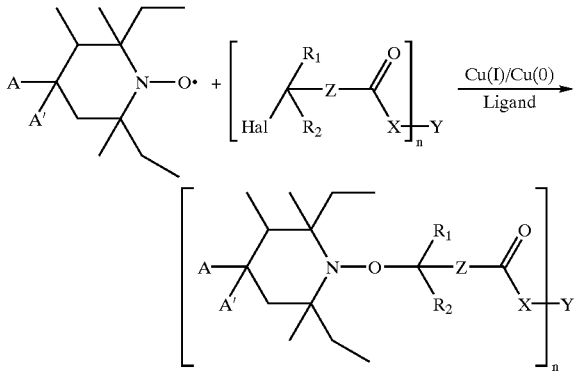

The nitroxyl compounds are known and can be prepared by known methods. Their preparation is for example described in GB 2335190, GB 2342649, and GB 2 361 235.

Hal is halogen and preferably Br or Cl.

Multifunctional halogenated compounds can be prepared for example by reacting a α-halogenated acid chloride or bromide with a polyfunctional alcohol, polyfunctional aminoalcohol, polyfunctional amine, polyfunctional mercaptane or polyfunctional phenol. The preparation of multifunctional halogenated compounds from polyfunctional alcohols and a α-halogenated acid chloride is for example described in WO 00/43344.

If X is a direct bond and Z is —O—CH$_2$—, then the the multifunctional compounds may be prepared for example by reacting a suitable derivative of a polycarboxylic acid, for example an acid chloride with the corresponding alcohol according the equation:

$$[Y{\pmb{\mathbf{+}}}_n\text{COCl} + \underset{\text{HO}}{\overset{R_1}{\bigg|}}\text{—Hal} \longrightarrow [Y{\pmb{\mathbf{+}}}_n\overset{O}{\overset{\|}{C}}\text{—O—}\underset{R_2}{\overset{R_1}{\bigg|}}\text{—Hal}$$

The above educts are reacted to the compounds according to formula Ia, Ib, Ic and Id in conventional solvents, such as for examples cyclic ethers in accordance with the method described by Matyjaszewski in U.S. Pat. No. 5,910,549.

A drawback of the process described in U.S. Pat. No. 5,910,549 is, that an excess of the nitroxyl compound has to be used which remains in the end product. A separation and purification is in most cases only possible by chromatography.

Since remaining nitroxyl radicals adversly affect the rate of the polymerization reaction, it is highly desirable to remove those radicals in an industrially feasible way. This problem has been solved by the present invention by applying a reducing step at the end of the reaction. The excess nitroxyl is reduced to the corresponding hydroxylamine or amine which both are more basic than the nitroxyl and thus can be washed out by an acid washing step.

Surprisingly the alkoxyamine remains unaffected and the yields remain high. The improvement is particularly useful in view of an industrial production of such compounds.

A further subject of the invention is therefore a process for the preparation of a compound of formula Ia, Ib, Ic or Id which process comprises the steps of a) reacting a compound of formula IIa, IIb, IIc or IId (IIa)

(IIb)

(IIc)

(IId)

with a compound of formula III $$\left[\underset{\text{Hal}}{\overset{R_1}{\bigg|}}\text{—Z—}\overset{O}{\overset{\|}{C}}\text{—X}\right]_n\text{—Y,} \quad \text{(III)}$$

having a radically transferable group Hal, with a transition metal complex in the absence of oxygen;

b) subjecting the reaction mixture to a reduction step;

c) washing the resulting mixture with an aqueous acid solution and d) isolating the product.

The definitions and preferences for the compounds of formula Ia, Ib, Ic and Id have already been given and apply also for the other subjects of the invention.

Complexing agents are known and for example described in U.S. Pat. No. 5,910,549.

The reduction step can be performed by various methods, such as for example by catalytic hydrogenation, with hydrazine or dithionite. Preferred is a reduction with Na-dithionite.

The Na-dithionite is preferably used as an aqueous solution or as a powder. The concentration of the aqueous solution may vary from 0.1% to 40% by weight, preferred is 5% to 20%.

The acid used in the washing step is preferably a mineral acid, such as HCl, but also organic sulfonic acids or complex acids such HPF$_8$ or HClO$_4$ are suitable.

The reaction temperature is preferably from 0° C. to 80° C., more preferably from 10° C. to 50° C.

The reaction time can vary in a wide range from 30 minutes to 24 hours, depending on the educts. In most cases 2 hours to 16 hours are sufficient to complete the reaction.

The reaction is usually carried out under normal conditions. However in some cases a slight pressure of up to 1 bar or a slight evacuation to 200 mbar may be of advantage.

The coupling reaction per se is known and the concentrations of the reactants may vary in a wide range as described in U.S. Pat. No. 5,910,549.

The following examples illustrate the invention.

A) PREPARATION EXAMPLES

Example A1

Compound 101

In a 100 ml three neck flask 7.75 g (36.1 mmol) 2,6-diethyl-2,3,6-trimethyl-4-hydroxy-piperidine-1-oxyl

19

(prepared according to DE 199 09 767 A1, example 2), 5.19 g (36.1 mmol) Cu(I)Br and 2.29 g (36.1 mmol) Cu(O)-powder are added. Oxygen is removed from the reaction mixture by applying vacuum and flushed with nitrogen. 50 ml dioxane and 6.0 g (18.1 mmol) 1,2-ethandiolbis(2-brompropionate) are added under stirring homogenized (suspension of CuBr and Cu in dissolved edukts). With a syringe 12.53 g (72.3 mmol) N,N,N',N'',N''-Pentamethyldiethylentriamine (PMDETA) are slowly added and the exothermal reaction started. The temperature is kept at 20° C. with an ice bath. During the reaction the color of the suspension changes from red to green. After 12 h stirring at 20° C. After stirring for 12 h at 20° C. the reaction is stopped and the reaction mixture is filtered over Tonsil Supreme 110FF (Süd Chemie). The filtrate is concentrated under vacuum and 50 ml aetylacetate are added: The solution is washed twice with 30 ml of a 10% EDTA-solution (ethylandiamin tetraacetic acid disodium salt), subsequently twice with 20 ml of a 10% freshly prepared sodium dithionite solution and finally once with 20 ml of a 0.1 n HCl. The organic phase is dried over $Na_2SO_4$, filtered off and the filtrate is concentrated and dried at 60° C. under vacuum. 6.7 g (62%) of compound 101 are obtained as a slightly yellow resinous product.

Elemental Analysis: Calculated $C_{32}H_{60}N_2O_8$: C 63.97%, H 10.07%, N 4.66%; Found: C 63.07%, H 10.05%, N 4.38%.

Example A2

Compound 102

In analogy to example A1 4.28 g (20 mmol) 2,6-diethyl-2,3,6-trimethyl-4-hydroxy-piperidine-1-oxyl, 2.87 g (20 mmol) Cu(I)Br, 1.27 g (20 mmol) Cu(O)-powder and 6.93 g (40 mmol) PMDETA are reacted in 40 ml dioxane with 4.14 g (10 mmol) 1,4-cyclohexandiolbis(2-brompropionate). 6.4 g (97%) of compound 102 are obtained as slightly yellow solid resin.

Elemental Analysis: Calculated $C_{38}H_{66}N_2O_8$: C 66.02%, H 10.16%, N 4.28%; Found: C 65.63%, H 10.04%, N 4.11%.

Example A3

Compound 103

In analogy to example 1 4.28 g (20 mmol) 2,6-diethyl-2,3,6-trimethyl-4-hydroxy-piperidine-1-oxyl, 2.87 g (20 mmol) Cu(I)Br, 1.27 g (20 mmol) Cu(O)-powder and 6.93 g (40 mmol) PMDETA are reacted in 40 ml dioxane with 3.86 g (10 mmol) N,N'-Bis-(2-brompropionyl)-1,6-diaminohexane. 5.5 g (84%) of compound 103 are obtained as white solid resin.

Elemental Analysis: Calculated $C_{38}H_{70}N_4O_6$: C 66.02%, H 10.77%, N 8.55%; Found: C 65.33%, H 10.70%, N 8.12%.

Example A4

Compound 104

In analogy to example 1 4.25 g (20 mmol) 2,6-diethyl-2,3,6-trimethyl-4-oxo-piperidine-1-oxyl, 2.87 g (20 mmol) Cu(I)Br, 1.27 g (20 mmol) Cu(O)-powder and 6.93 g (40 mmol) PMDETA are reacted in 40 ml dioxane with 3.86 g (10 mmol) N,N'-Bis-(2-brompropionyl)-1,6-diaminohexane. 5.6 g (85%) of compound 104 are obtained as pale white solid resin.

20

Elemental Analysis: Calculated $C_{38}H_{70}N_4O_6$: C 66.43%, H 10.22%, N 8.61%; Found: C 66.01%, H 9.90%, N 8.22%.

Example A5

Compound 105

In analogy to example 1 4.28 g (20 mmol) 2,6-diethyl-2,3,6-trimethyl-4-hydroxy-piperidine-1-oxyl, 2.87 g (20 mmol) Cu(I)Br, 1.27 g (20 mmol) Cu(O)-powder and 6.93 g (40 mmol) PMDETA are reacted in 40 ml dioxane with 6.24 g (10 mmol) poly(ethylene glycole-400)-bis(2-brompropionate). 5.7 g (67%) of compound 105 are obtained as pale white solid resin.

Example A6

Compound 106

In analogy to example 1 4.28 g (20 mmol) 2,6-diethyl-2,3,6-trimethyl-4-hydroxy-piperidine-1-oxyl, 2.87 g (20 mmol) Cu(I)Br, 1.27 g (20 mmol) Cu(O)-powder and 6.93 g (40 mmol) PMDETA are reacted in 40 ml dioxane with 6.24 g (10 mmol) poly(tetrahydrofuran-250)-bis(2-brompropionate). 6.1 g (77%) of compound 106 are obtained as pale white solid resin.

Example A7

Compound 107

In analogy to example A1 3.21 g (15 mmol) 2,6-Diethyl-2,3,6-trimethyl-4-hydroxy-piperidine-1-oxyl, 2.15 g (15 mmol) Cu(I)Br, 191 mg (3 mmol) Cu(O)-powder and 2.60 g (0.15 mmol) PMDETA are reacted in 15 ml ethylacetate with 2.69 g (5 mmol) tris-(2'-brompropionyl)-1,1,1-trimethylolpropane (prepared according to WO 00/43344) for 20 h at R.T. 2.42 g (51%) of compound 108 are obtained as a white powder.

Elemental Analysis: Calculated $C_{51}H_{95}N_3O_{12}$: C 65.01%, H 10.16%, N 4.46%; Found: C 63.69%, H 9.86%, N 4.40%. Maldi-TOF-MS: $M^+$: 942 (as calculated).

Example A8

Compound 108

In analogy to example 1 3.21 g (15 mmol) 2,6-diethyl-2,3,6-trimethyl-4-hydroxy-piperidine-1-oxyl, 2.15 g (15 mmol) Cu(I)Br, 191 mg (3 mmol) Cu(O)-powder and 2.60 g (15 mmol) PMDETA in 15 ml ethylacetate are reacted with 2.86 g (5 mmol) Tris-(2'-brompropionyl)phloroglucine (prepared in accordance with WO 00/43344) for 18 h at R.T. 4.05 g (83%) of compound 109 are obtained as a white orange powder.

Example A9

Compound 109

In analogie to example 1 4.28 g (20 mmol) 2,6-Diethyl-2,3,6-trimethyl-4-hydroxy-piperidine-1-oxyl, 2.87 g (20 mmol) Cu(I)Br, 318 mg (5 mmol) Cu(O)-powder and 3.46 g (20 mmol) PMDETA in 15 ml ethylacetate are reacted with 3.38 g (5 mmol) tetrakies-(2'-brompropionyl)-pentaerythrite (prepared in accordance with WO 00/43344) umgesetzt (20 h, R.T.). 4.75 g (78%) of compound 110 are obtained as a white powder.

Elemental Analysis: Calculated $C_{65}H_{120}N_4O_{16}$: C 64.38%, H 9.97%, N 4.62%; Found: C 63.75%, H 9.76%, N 4.49%. Maldi-TOF-MS: $M^+$: 1213 (as calculated).

Example A10

Compound 110

In analogy to example 1 2.57 g (12 mmol) 2,6-diethyl-2,3,6-trimethyl-4-hydroxy-piperidine-1-oxyl, 1.18 g (12 mmol) Cu(I)Cl, 152 mg (2.4 mmol) Cu(O)-powder and 2.08 g (12 mmol) PMDETA in 15 ml ethylacetate are reacted with 1.45 g (2 mmol) Hexakis-(2'-chlorpropionyl)sorbitol (prepared in accordance with WO 00/43344) for 15 h at R.T. 3.0 g (84%) of compound 111 are obtained as an off white powder.

Elemental Analysis: Calculated $C_{96}H_{176}N_6O_{24}$: C 64.11%, H 9.86%, N 4.67%; Found: C 63.20%, H 9.57%, N 4.25%.

Example A111

Compound 111

In analogy to example A1 3.06 g (12 mmol) 1-t-butyl-3,3-diethyl-5,5-dimethylpiperazin-2-on-4-oxyl (prepared in accordance with DE 19949352 A1, example B38), 1.72 g (12 mmol) Cu(I)Br, 0.76 g (12 mmol) Cu(O)-powder and 4.24 g (24 mmol) PMDETA are reacted in 25 ml toluene with 1.99 g (6 mmol) 1,2-ethandiolbis(2-brompropionate). 1.96 g (48%) of compound 111 are obtained as a colorless resinous product.

Elemental Analysis: Calculated $C_{38}H_{88}N_4O_8$; C 63.31%, H 9.74%, N 8.20%; Found: C 63.09%, H 9.58%, N 7.77%.

Example A112

Compound 112

In analogy to example A1 5.0 g (25 mmol) 3,3-diethyl-5,5 dimethylmorpholin-2-on-4-oxyl (prepared in accordance with DE 19949352 A1, example B8), 3.70 g (25 mmol) Cu(I)Br, 1.60 g (25 mmol) Cu(O)-powder and 8.84 g (50 mmol) PMDETA are reacted in 50 ml toluene with 4.15 g (12.5 mmol) 1,2-ethandiolbis(2-brompropionate). 6.57 g (92%) of compound 112 are obtained as a colorless resinous product.

Elemental Analysis: Calculated $C_{28}H_{48}N_2O_{10}$; C 58.72%, H 8.45%, N 4.89%; Found: C 58.98%, H 8.46%, N 4.78%.

The compounds are summarized in Table 1.

TABLE 1

Compounds prepared

| Compound no. | Structure |
|---|---|
| 101 | 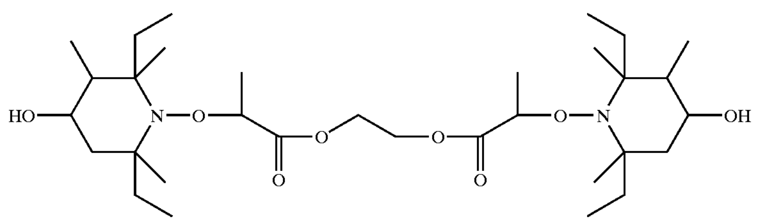 |
| 102 | 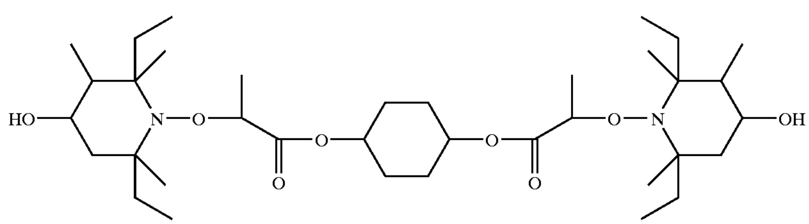 |
| 103 | 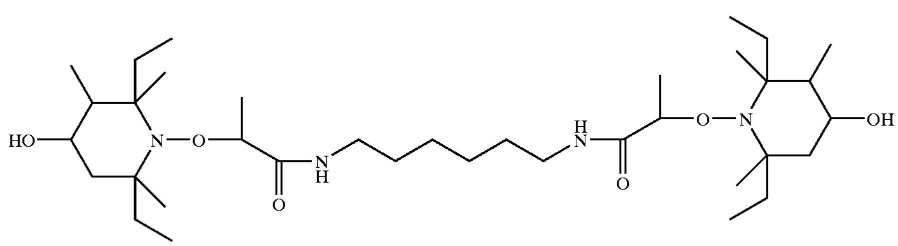 |
| 104 | 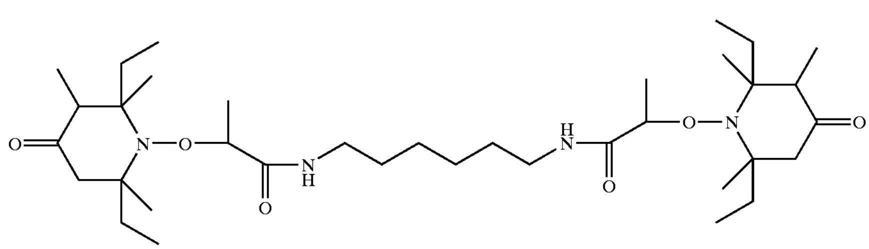 |

TABLE 1-continued
Compounds prepared
Compound no. Structure
105 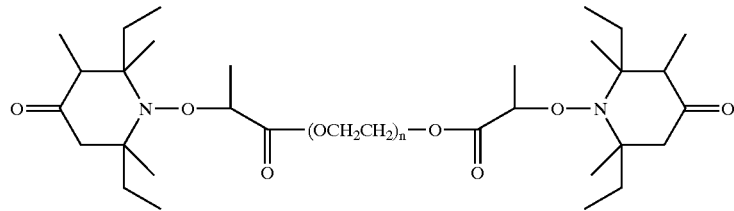
(PEG400)
106 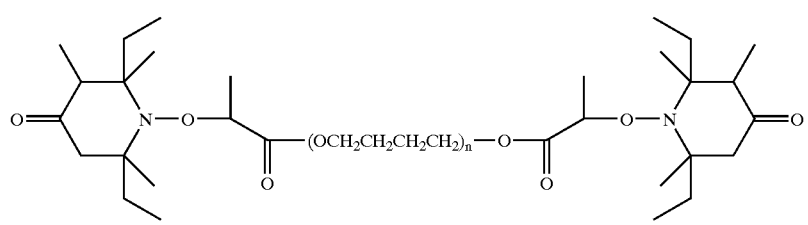
(PTHF 250)
107 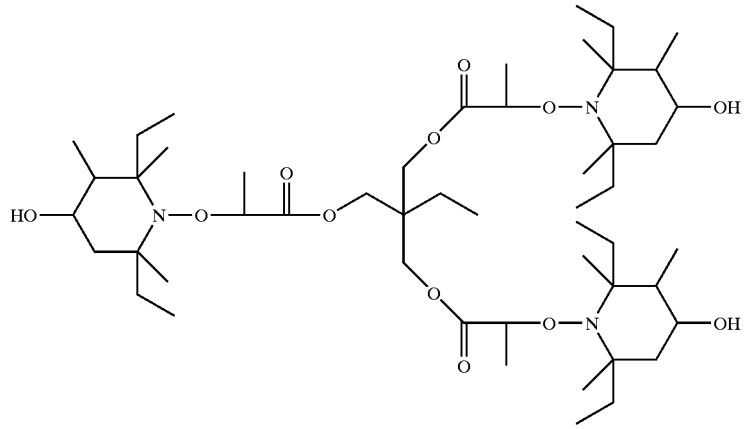
108 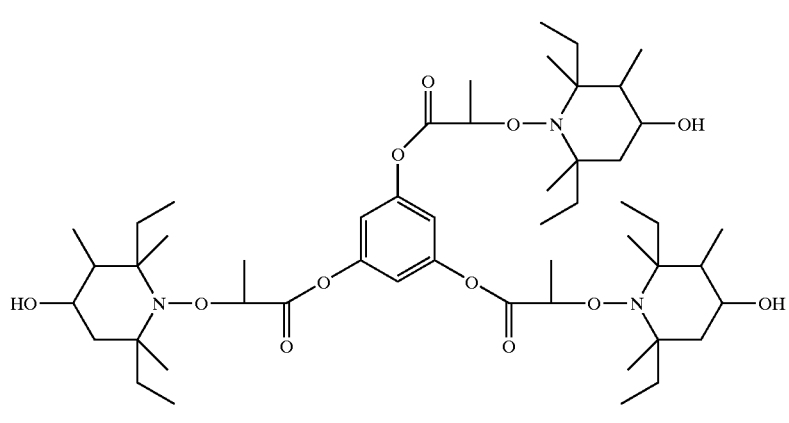

TABLE 1-continued
Compounds prepared
Compound no. Structure
109 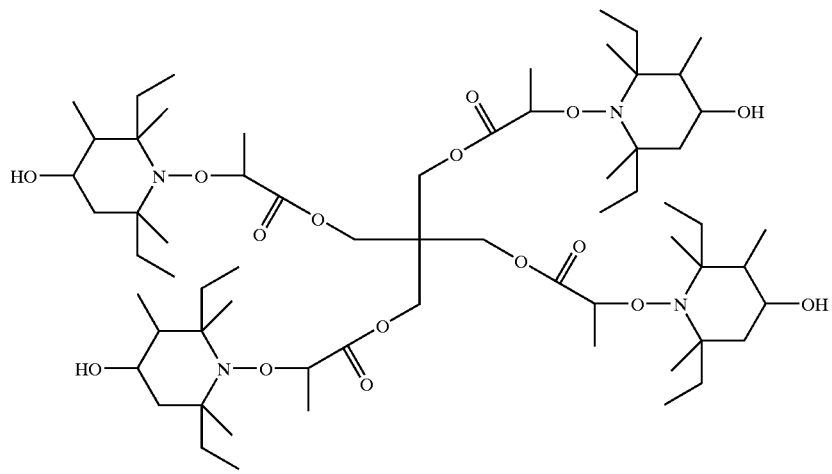
110 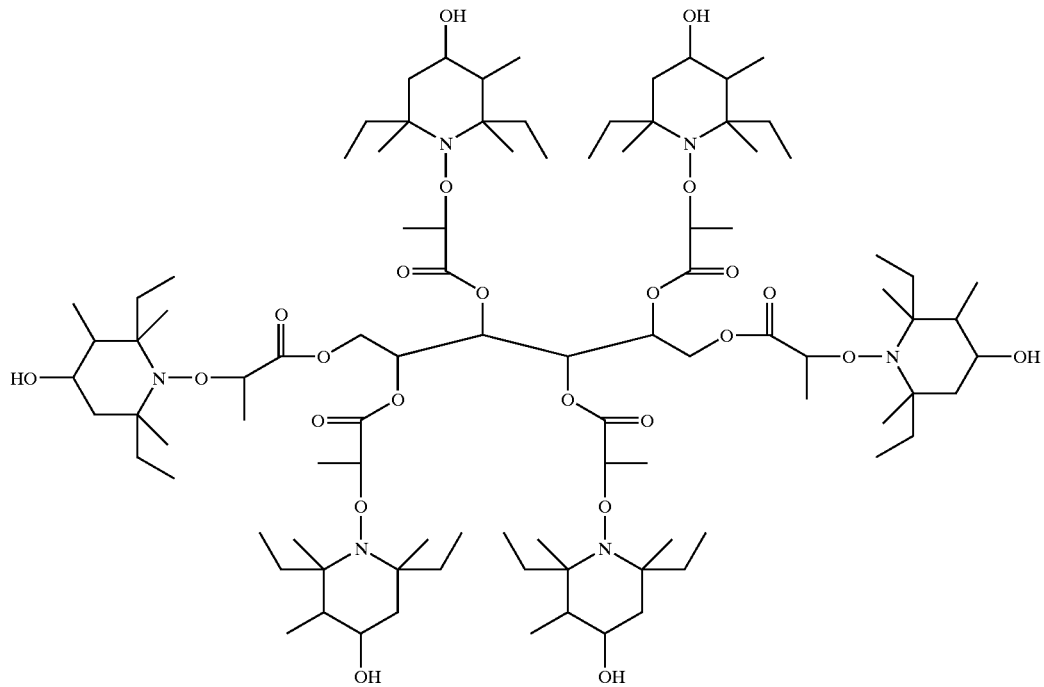
111 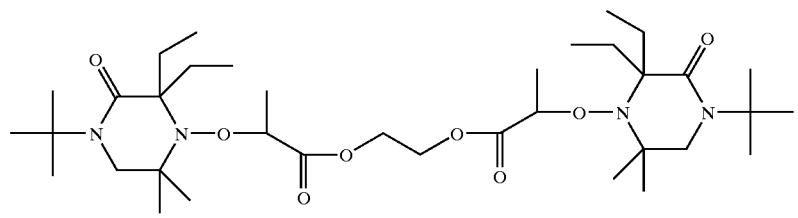

TABLE 1-continued

Compounds prepared

Compound no. Structure

112

B POLYMERIZATION EXAMPLES

Polymerization Examples in Styrene

General Remarks:

Styrene and the other monomers are distilled over a Vigreux column under vacuum, shortly before being used.

To remove oxygen all polymerization reaction mixtures are flushed before polymerization with argon and evacuated under vaccum applying a freeze-thaw cycle. The reaction mixtures are then polymerized under argon atmosphere.

At the start of the polymerization reaction, all starting materials are homogeneously dissolved.

Conversion is determined by removing unreacted monomers from the polymer in a vacuum oven at 70° C. and 0.01 torr for at least 24 hours, weighing the remaining polymer and subtracting the weight of the initiator.

Characterization of the polymers is carried out by GPC (Gel Permeation Chromatography).

GPC: Is performed using RHEOS 4000 of FLUX INSTRUMENTS. Tetrahydrofuran (THF) is used as a solvent and is pumped at 1 ml/min. Two chromatography columns are put in series: type Plgel 5 μm mixed-C of POLYMER INSTRUMENTS, Shropshire, UK. Measurements are performed at 40° C. The columns are calibrated with low polydispersity polystyrenes having Mn from 200 to 2 000 000 Dalton. Detection is carried out using a RI-Detector or UV-Detector at 30° C.

Example B1

Polymerization of Styrene with 0.5 mol % of Compound 102 (Table 1) at 130° C.

In a 100 ml schlenck flask, equipped with magnetic stirrer, 0.972 g (1.48 mmol) of compound 102 and 30.9 g (297 mmol) of styrene are mixed and degassed. The clear solution obtained is stirred under argon at 130° C. and polymerization is carried out during 6 h. The reaction mixture is then cooled to RT. The remaining monomer is removed by evaporation under high vacuum at 70° C. 21.8 g (70.6%) of the initial monomer have reacted. A slightly yellow solid is obtained.

Mn=13780, Mw=17360, PD=1.26

Example B2

Polymerization of Styrene with 0.5 mol % of Compound 103 (Table 1) at 130° C.

In a 100 ml schlenck flask, equipped with magnetic stirrer, 0.974 g (1.49 mmol) of compound 103 and 31.0 g (297 mmol) of styrene are mixed and degassed. The clear solution obtained is stirred under argon at 130° C. and polymerization is carried out during 6 h. The reaction mixture is then cooled to RT. The remaining monomer is removed by evaporation under high vacuum at 70° C. 22.7 g (73.4%) of the initial monomer have reacted. A white solid is obtained.

Mn=1520, Mw=23980, PD=1.58

Example B3

Polymerization of Styrene with 0.5 mol % of Compound 104 (Table 1) at 130° C.

In a 100 ml schlenck flask, equipped with magnetic stirrer, 0.525 g (0.81 mmol) of compound 104 and 16.8 g (161 mmol) of styrene are mixed and degassed. The clear solution obtained is stirred under argon at 130° C. and polymerization is carried out during 6 h. The reaction mixture is then cooled to RT. The remaining monomer is removed by evaporation under high vacuum at 70° C. 13.1 g (78.1%) of the initial monomer have reacted. A white solid is obtained.

Mn=17420, Mw=25550, PD=1.47

Polymerization Examples in Acrylates

Example B4

Polymerization of n-BuA with Compound 102 (Table 1)

A round-bottom three necked flask, equipped with thermometer, condenser and magnetic stirrer is charged with 0.383 g (0.59 mmol) of compound 102 and 10 g (78 mmol) of n-butylacrylate and degassed. The clear solution is then heated to 145° C. under argon. The mixture is stirred for 5 hours at 145° C. and then cooled to 60° C. and the remaining monomer is evaporated under high vacuum. 7.9 g (79%) of the monomer are reacted and a yellow turbid viscous liquid is obtained.

GPC: Mn=11000, Mw=15070, Polydispersity index=1.37

Example B5

Polymerization of n-BuA with Compound 103 (Table 1)

A round-bottom three necked flask, equipped with thermometer, condenser and magnetic stirrer is charged with 0.383 g (0.59 mmol) of compound 103 and 10 g (78 mmol) of n-butylacrylate and degassed. The clear solution is then heated to 145° C. under argon. The mixture is stirred for 5 hours at 145° C. and then cooled to 60° C. and the remaining monomer is evaporated under high vacuum. 7.9 g (79%) of the monomer are reacted and a yellow viscous liquid is obtained.

GPC: Mn=11650, Mw=17475, Polydispersity index=1.5

Example B6

Polymerization of n-BuA with Compound 111

A round-bottom three necked flask, equipped with thermometer, condenser and magnetic stirrer is charged with 0,403 g (0.59 mmol) of compound 111 and 10 g (78 mmol) of n-buthylacrylate and degassed. The clear solution is then heated to 145° C. under argon. The mixture is stirred for 5 hours at 145° C. and then cooled to 60° C. and the remaining monomer is evaporated under high vacuum. 7.2 g (72%) of the monomer are reacted and a yellow viscous liquid is obtained.

GPC: Mn=9710, Mw=12050, polydispersity index PD=1.24

Example B7

Polymerization of n-BuA with Compound 112

A round-bottom three necked flask, equipped with thermometer, condenser and magnetic stirrer is charged with 0.338 g (0.59 mmol) of compound 112 and 10 g (78 mmol) of n-buthylacrylate and degassed. The clear solution is then heated to 145° C. under argon. The mixture is stirred for 5 hours at 145° C. and then cooled to 60° C. and the remaining monomer is evaporated under high vacuum. 7.8 g (78%) of the monomer are reacted and a yellow viscous liquid is obtained.

GPC: Mn=9890, Mw=12960, polydispersity index PD=1.31

What is claimed is:

1. A compound of formula Ia, Ib, Ic or Id

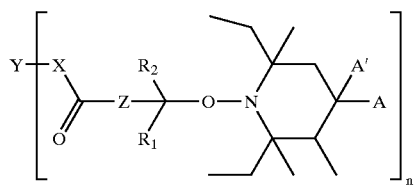

(Ia)

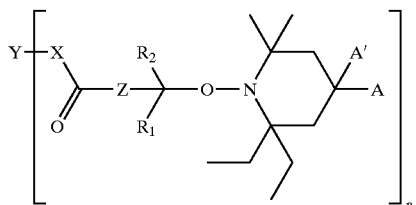

(Ib)

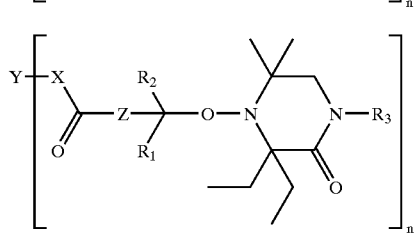

(Ic)

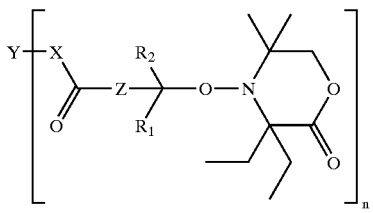

(Id)

wherein $R_1$ and $R_2$ are independently of each other hydrogen, $C_1$–$C_{18}$alkyl or phenyl;

$R_3$ is hydrogen, $C_1$–$C_{18}$alkyl, $C_1$–$C_{18}$alkyl which is substituted by OH, or phenyl which is unsubstituted or substituted by OH, halogen, $C_1$–$C_8$alkoxy or $C_1$–$C_8$alkyl;

X is O, S, $NR_4$ or, if Z is —O—$CH_2$—, X is additionally a direct bond;

$R_4$ is hydrogen or $C_1$–$C_{18}$alkyl;

Z is a direct bond or, if $R_1$ is hydrogen and $R_2$ phenyl, Z is additionally —O—$CH_2$—;

Y is a radical derived from a polyol, a polyamine, a polyaminoalcohol, a polyaminothiol, a polyhydroxythiol, a polyaminohydroxythiol or a polythiol having 2 to 20 —OH, SH and/or —$NR_5H$ groups, wherein $R_5$ is hydrogen, $C_1$–$C_{18}$alkyl or phenyl;

or if X is a direct bond and Z is —O—$CH_2$—, Y is a radical derived from a polycarboxylic acid having 2–20 carboxylic functions;

A and A' together are =O; or

A' is hydrogen; and

A is hydrogen, —O—$R_{100}$, wherein $R_{100}$ is hydrogen, $C_1$–$C_{18}$alkyl which is uninterrupted or interrupted by one or more oxygen atoms, $NHR_{100}$, $NR_{100}R_{103}$ or cyanoethyl;

or is a group

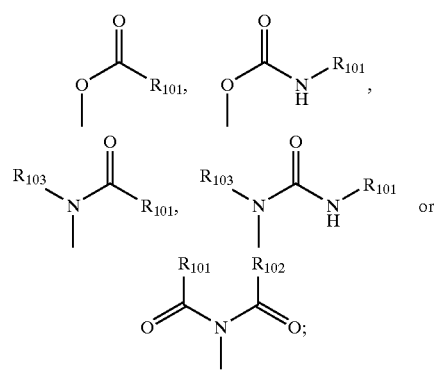

$R_{101}$ is hydrogen, —COOH, —COO($C_1$–$C_4$alkyl), —COO-phenyl, —COObenzyl, $C_1$–$C_8$alkoxy, $C_1$–$C_{18}$alkyl, $C_2$–$C_4$alkenyl, $C_1$–$C_{18}$alkyl or $C_2$–$C_4$alkenyl substituted by OH, —COOH or —COO ($C_1$–$C_4$)alkyl, $C_2$–$C_{18}$alkyl which may be interrupted by one or more oxygen atoms, unsubstituted cyclopentyl, cyclohexyl, cyclohexenyl, phenyl or naphthyl; or cyclopentyl, cyclohexyl, cylohexenyl, phenyl or naphthyl which are substituted by $C_1$–$C_4$alkyl, —COOH or —COO—($C_1$–$C_4$alkyl);

$R_{102}$ is hydrogen or $C_1$–$C_{18}$alkyl or $R_{101}$ and $R_{102}$ together with the nitrogen atom form a 5-membered ring which may have an unsaturated bond or be fused to a benzene ring;

$R_{103}$ is hydrogen or $C_1$–$C_{18}$alky; or

A and A' together are a group

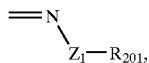

wherein $Z_1$ is O or $NR_{202}$, or when $R_{201}$ represents alkyl or aryl, $Z_1$ is additionally a direct bond;

$R_{202}$ is H, $C_1$–$C_{18}$alkyl or phenyl;

$R_{201}$ is H, straight or branched $C_1$–$C_{18}$alkyl or $C_3$–$C_{18}$alkenyl, which may be unsubstituted or substituted, by one or more OH, $C_1$–$C_8$alkoxy, carboxy, $C_1$–$C_8$alkoxycarbonyl, $C_5C_{12}$cycloalkyl or $C_5$–$C_{12}$cycloalkenyl groups; phenyl, $C_7$–$C_9$phenylalkyl or naphthyl which may be unsubstituted or substituted by one or more $C_1$–$C_8$alkyl, halogen, OH, $C_1$–$C_8$alkoxy, carboxy or $C_1$–$C_8$alkoxycarbonyl groups; or —C(O)—$C_1$–$C_{18}$alkyl, or an acyl moiety of a α,β-unsaturated carboxylic acid having 3 to 9 carbon atoms or of an aromatic carboxylic acid having 7 to 15 carbon atoms; —$SO_3^-Me^+$, —$PO(O^-Me^+)_2$, —$P(O)(OR_2)_2$, —$SO_2R_2$, —CO—NH—$R_2$, —$CONH_2$, $COOR_2$, or $Si(Me)_3$, wherein $Me^+$ is =$H^+$, ammonium or an alkali metal cation; or A is O—$Y_1$ and A' is O—$Y_2$ forming a ketal structure in the 4 position; wherein $Y_1$ and $Y_2$ are independently $C_1$–$C_{12}$alkyl, $C_3$–$C_{12}$alkenyl, $C_3$–$C_{12}$alkinyl, $C_5$–$C_8$cycloalkyl, phenyl, naphthyl or $C_7$–$C_9$phenylalkyl; or $Y_1$ and $Y_2$ together form one of the bivalent groups —$C(R_{301})(R_{302})$—$CH(R_{303})$—, —$CH(R_{301})$—$CH_2$—$C(R_{302})(R_{303})$—, —$CH(R_{302})$—$CH_2$—$C(R_{301})(R_{303})$—, —$CH_2$—$C(R_{301})(R_{302})$—$CH(R_{303})$—, o-phenylene, 1,2-cyclohexylidene, —$CH_2$—CH=CH—$CH_2$— or

wherein $R_{301}$ is hydrogen, $C_1$–$C_{12}$alkyl, COOH, COO—$(C_1$–$C_{12})$alkyl or $CH_2OR_{304}$;

$R_{302}$ and $R_{303}$ are independently hydrogen, methyl, ethyl, COOH or COO—$(C_1$–$C_{12})$alkyl; and $R_{304}$ is hydrogen, $C_1$–$C_{12}$alkyl, benzyl or a monovalent acyl residue derived from an aliphatic, cycloaliphatic or aromatic monocarboxylic acid having up to 18 carbon atoms; and n is a number from 2–20.

2. A compound of formula Ia, Ib, Ic or Id according to claim 1 wherein

X is O or $NR_4$, wherein $R_4$ is hydrogen or $C_1$–$C_8$alkyl;

Z is a direct bond;

$R_1$ is hydrogen or $C_1$–$C_{18}$alkyl; and $R_2$ is $C_1$–$C_{18}$alkyl.

3. A compound of formula Ia, Ib, Ic or Id according to claim 1 wherein

A and A' together are =O; or

A' is hydrogen and

A is hydrogen, OH, $OR_{100}$, $NHR_{100}$, $NR_{100}R_{103}$ or a group

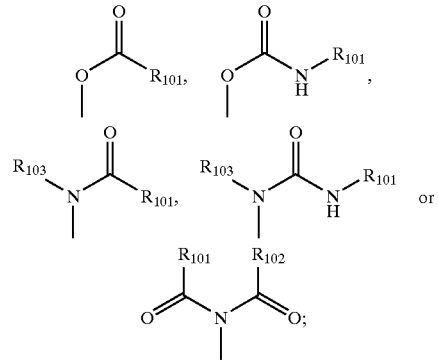

wherein $R_{100}$, $R_{101}$, $R_{102}$ and $R_{103}$ independently are hydrogen or $C_1$–$C_{18}$alkyl; or A is O—Y, and A' is O—$Y_2$ forming a ketal structure in the 4 position; wherein $Y_1$ and $Y_2$ are independently $C_1$–$C_{12}$alkyl, phenyl or benzyl; or $Y_1$ and $Y_2$ together form one of the bivalent groups —$C(R_{301})(R_{302})$—$CH(R_{303})$—, $CH(R_{301})$—$CH_2$—C $(R_{302})(R_{303})$—, —$CH(R_{302})$—$CH_2$—$C(R_{301})(R_{303})$—, —$CH_2$—$C(R_{301})(R_{302})$—$CH(R_{303})$—, or —$CH_2$—CH=CH—$CH_2$—, wherein $R_{301}$ is hydrogen, $C_1$–$C_{12}$alkyl or COO—$(C_1$–$C_{12})$alkyl; and $R_{302}$ and $R_{303}$ are independently hydrogen, methyl ethyl or COO—$(C_1$–$C_{12})$alkyl.

4. A compound of formula Ia, Ib, Ic or Id according to claim 1 wherein Y is a radical derived from a polyol or a polyamine having 2 to 20 —OH or —$NR_5H$ groups, wherein $R_5$ is hydrogen, $C_3$–$C_{18}$alkyl or phenyl.

5. A compound of formula Ia, Ib, Ic or Id according to claim 4 wherein Y is an aliphatic polyol.

6. A compound of formula Ia, Ib, Ic or Id according to claim 1 wherein n is a number from 2–10.

7. A compound of formula Ia, Ib, Ic or Id according to claim 6 wherein n is a number from 2 to 6.

8. A compound of formula Ia or Ib according to claim 1.

9. A polymerizable composition, comprising a) at least one ethylenically unsaturated monomer or oligomer, and b) a compound of formula Ia, Ib, Ic or Id or a mixture thereof

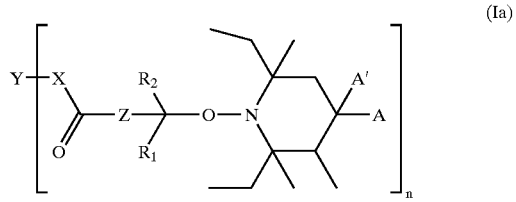

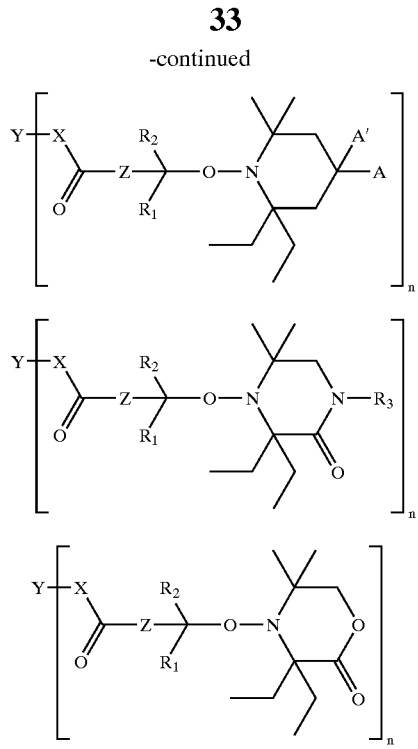

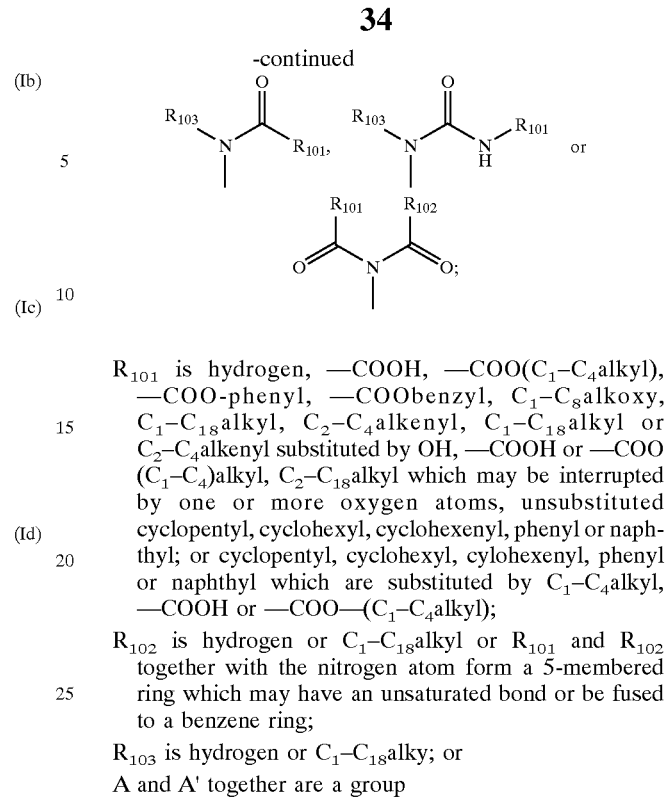

wherein

- $R_1$ and $R_2$ are independently of each other hydrogen, $C_1$–$C_{18}$alkyl or phenyl;
- $R_3$ is hydrogen, $C_1$–$C_{18}$alkyl, $C_1$–$C_{18}$alkyl which is substituted by OH, or phenyl which is unsubstituted or substituted by OH, halogen, $C_1$–$C_8$alkoxy or $C_1$–$C_8$alkyl;
- X is O, S, $NR_4$ or, if Z is —O—$CH_2$—, X is additionally a direct bond;
- $R_4$ is hydrogen or $C_1$–$C_{18}$alkyl;
- Z is a direct bond or, if $R_1$ is hydrogen and $R_2$ phenyl, Z is additionally —O—$CH_2$—;
- Y is a radical derived from a polyol, a polyamine, a polyaminoalcohol, a polyaminothiol, a polyhydroxythiol, a polyaminohydroxythiol or a polythiol having 2 to 20 —OH, SH and/or —$NR_5$H groups, wherein $R_5$ is hydrogen, $C_1$–$C_{18}$alkyl or phenyl;
- or if X is a direct bond and Z is —O—$CH_2$—, Y is a radical derived from a polycarboxylic acid having 2–20 carboxylic functions;
- A and A' together are =O; or
- A' is hydrogen; and
- A is hydrogen, —O—$R_{100}$, wherein $R_{100}$ is hydrogen, $C_1$–$C_{18}$alkyl which is uninterrupted or interrupted by one or more oxygen atoms, $NHR_{100}$, $NR_{100}R_{103}$ or cyanoethyl;
- or is a group

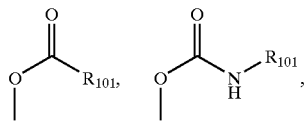

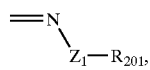

- $R_{101}$ is hydrogen, —COOH, —COO($C_1$–$C_4$alkyl), —COO-phenyl, —COObenzyl, $C_1$–$C_8$alkoxy, $C_1$–$C_{18}$alkyl, $C_2$–$C_4$alkenyl, $C_1$–$C_{18}$alkyl or $C_2$–$C_4$alkenyl substituted by OH, —COOH or —COO ($C_1$–$C_4$)alkyl, $C_2$–$C_{18}$alkyl which may be interrupted by one or more oxygen atoms, unsubstituted cyclopentyl, cyclohexyl, cyclohexenyl, phenyl or naphthyl; or cyclopentyl, cyclohexyl, cylohexenyl, phenyl or naphthyl which are substituted by $C_1$–$C_4$alkyl, —COOH or —COO—($C_1$–$C_4$alkyl);
- $R_{102}$ is hydrogen or $C_1$–$C_{18}$alkyl or $R_{101}$ and $R_{102}$ together with the nitrogen atom form a 5-membered ring which may have an unsaturated bond or be fused to a benzene ring;
- $R_{103}$ is hydrogen or $C_1$–$C_{18}$alky; or
- A and A' together are a group $$=N\underset{Z_1-R_{201},}{\diagdown}$$

wherein

- $Z_1$ is O or $NR_{202}$, or when $R_{201}$ represents alkyl or aryl, $Z_1$ is additionally a direct bond;
- $R_{202}$ is H, $C_1$–$C_{18}$alkyl or phenyl;
- $R_{201}$ is H, straight or branched $C_1$–$C_{18}$alkyl or $C_3$–$C_{18}$alkenyl, which may be unsubstituted or substitued, by one or more OH, $C_1$–$C_8$alkoxy, carboxy, $C_1$–$C_8$alkoxycarbonyl, $C_5$–$C_{12}$cycloalkyl or $C_5C_{12}$cycloalkenyl groups; phenyl, $C_7$–$C_9$phenylalkyl or naphthyl which may be unsubstituted or substituted by one or more $C_1$–$C_8$alkyl, halogen, OH, $C_1$–$C_8$alkoxy, carboxy or $C_1$–$C_8$alkoxycarbonyl groups; or —C(O)—$C_1$–$C_{18}$alkyl, or an acyl moiety of a α,β-unsaturated carboxylic acid having 3 to 9 carbon atoms or of an aromatic carboxylic acid having 7 to 15 carbon atoms;
- —$SO_3^-Me^+$, —$PO(O^-Me^+)_2$, —$P(O)(OR_2)_2$, —$SO_2R_2$, —CO—NH—$R_2$, —$CONH_2$, $COOR_2$, or $Si(Me)_3$, wherein $Me^+$ is =$H^+$, ammonium or an alkali metal cation; or
- A is O—$Y_1$ and A' is O—$Y_2$ forming a ketal structure in the 4 position; wherein
- $Y_1$ and $Y_2$ are independently $C_1$–$C_{12}$alkyl, $C_3$–$C_{12}$alkenyl, $C_3$–$C_{12}$alkinyl, $C_5$–$C_8$cycloalkyl, phenyl, naphthyl or $C_7$–$C_9$phenylalkyl; or
- $Y_1$ and $Y_2$ together form one of the bivalent groups —C($R_{301}$)($R_{302}$)—CH($R_{303}$)—, —CH($R_{301}$)—$CH_2$—C($R_{302}$)($R_{303}$)—, —CH($R_{302}$)—$CH_2$—C($R_{301}$)($R_{303}$)—, —$CH_2$—C($R_{301}$)($R_{302}$)—CH($R_{303}$)—, o-phenylene, 1,2-cyclohexylidene, —$CH_2$—CH=CH—$CH_2$— or

wherein

R$_{301}$ is hydrogen, C$_1$–C$_{12}$alkyl, COOH, COO—(C$_1$–C$_{12}$)alkyl or CH$_2$OR$_{304}$;

R$_{302}$ and R$_{303}$ are independently hydrogen, methyl, ethyl, COOH or COO—(C$_1$–C$_{12}$)alkyl; and R$_{304}$ is hydrogen, C$_1$–C$_{12}$alkyl, benzyl or a monovalent acyl residue derived from an aliphatic, cycloaliphatic or aromatic monocarboxylic acid having up to 18 carbon atoms; and n is a number from 2–20.

10. A composition according to claim 9, wherein the ethylenically unsaturated monomer or oligomer is selected from the group consisting of ethylene, propylene, n-butylene, i-butylene, styrene, substituted styrene, conjugated dienes, acrolein, vinyl acetate, vinylpyrrolidone, vinylimidazole, maleic anhydride, (alkyl)acrylic acidanhydrides, (alkyl)acrylic acid salts, (alkyl)acrylic esters, (meth)acrylonitriles, (alkyl)acrylamides, vinyl halides and vinylidene halides.

11. A composition according to claim 9, wherein the ethylenically unsaturated monomers are ethylene, propylene, n-butylene, i-butylene, isoprene, 1,3-butadiene, α-C$_5$–C$_{18}$alkene, styrene, α-methyl styrene, p-methyl styrene or a compound of formula CH$_2$=C(R$_a$)—(C=Z)—R$_b$, wherein R$_a$ is hydrogen or C$_1$–C$_4$alkyl, R$_b$ is NH$_2$, O$^-$(Me$^+$), glycidyl, unsubstituted C$_1$–C$_{18}$alkoxy, C$_2$–C$_{100}$alkoxy interrupted by at least one N and/or O atom, hydroxy-substituted C$_1$–C$_{18}$alkoxy, unsubstituted C$_1$–C$_{18}$alkylamino, di(C$_1$–C$_{48}$alkyl)amino, hydroxy-substituted C$_1$–C$_{18}$alkylamino or hydroxy-substituted di(C$_1$–C$_{18}$alkyl)amino, —O—CH$_2$CH$_2$N(CH$_3$)$_2$ or —O—CH$_2$—CH$_2$—N$^+$H(CH$_3$)$_2$ An$^-$;

An$^-$ is an anion of a monovalent organic or inorganic acid;

Me is a monovalent metal atom or the ammonium ion and

Z is oxygen or sulfur.

12. A composition according to claim 9, wherein the compound of formula Ia, Ib, Ic or Id is present in an amount of from 0.01 mol-% to 20 mol-%.

13. A process for preparing an oligomer, a cooligomer, a polymer or a copolymer (block or random) by free radical polymerization of at least one ethylenically unsaturated monomer or oligomer, which comprises (co)polymerizing the monomers or oligomers in the presence of an initiator compound of formula Ia, Ib, Ic or Id under reaction conditions capable of effecting scission of the O—C bond to form two free radicals, the radical

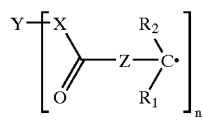

being capable of initiating polymerization, wherein the compounds of formula Ia, Ib, Ic or Id are

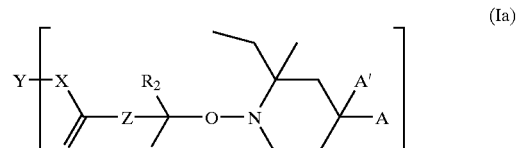

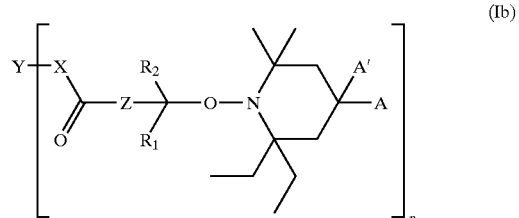

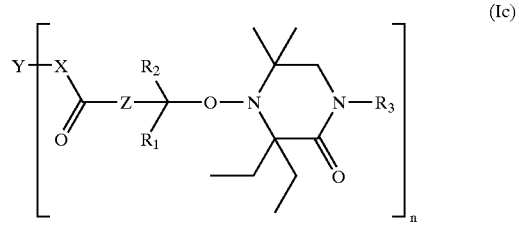

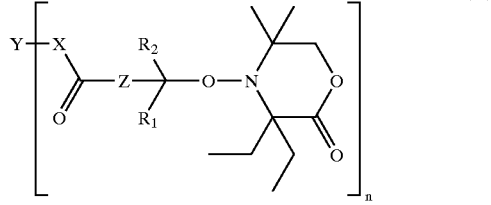

wherein

R$_1$ and R$_2$ are independently of each other hydrogen, C$_1$–C$_{18}$alkyl or phenyl;

R$_3$ is hydrogen, C$_1$–C$_{18}$alkyl, C$_1$–C$_{18}$alkyl which is substituted by OH, or phenyl which is unsubstituted or substituted by OH, halogen, C$_1$–C$_8$alkoxy or C$_1$–C$_8$alkyl;

X is O, S, NR$_4$ or, if Z is —O—CH$_2$—, X is additionally a direct bond;

R$_4$ is hydrogen or C$_1$–C$_{18}$alkyl;

Z is a direct bond or, if R$_1$ is hydrogen and R$_2$ phenyl, Z is additionally —O—CH$_2$—;

Y is a radical derived from a polyol, a polyamine, a polyaminoalcohol, a polyaminothiol, a polyhydroxythiol, a polyaminohydroxythiol or a polythiol having 2 to 20 —OH, SH and/or —NR$_5$H groups, wherein R$_5$ is hydrogen, C$_1$–C$_{18}$alkyl or phenyl;

or if X is a direct bond and Z is —O—CH$_2$—, Y is a radical derived from a polycarboxylic acid having 2–20 carboxylic functions;

A and A' together are =O; or

A' is hydrogen; and

A is hydrogen, —O—$R_{100}$, wherein $R_{100}$ is hydrogen, $C_1$–$C_{18}$alkyl which is uninterrupted or interrupted by one or more oxygen atoms, $NHR_{100}$, $NR_{100}R_{103}$ or cyanoethyl;
or is a group

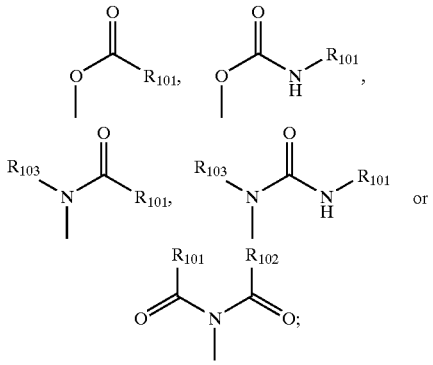

$R_{101}$ is hydrogen, —COOH, —COO($C_1$–$C_4$alkyl), —COO-phenyl, —COObenzyl, $C_1$–$C_8$alkoxy, $C_1$–$C_{18}$alkyl, $C_2$–$C_4$alkenyl, $C_1$–$C_{18}$alkyl or $C_2$–$C_4$alkenyl substituted by OH, —COOH or —COO($C_1$–$C_4$)alkyl, $C_2$–$C_{18}$alkyl which may be interrupted by one or more oxygen atoms, unsubstituted cyclopentyl, cyclohexyl, cyclohexenyl, phenyl or naphthyl; or cyclopentyl, cyclohexyl, cylohexenyl, phenyl or naphthyl which are substituted by $C_1$–$C_4$alkyl, —COOH or —COO—($C_1$–$C_4$alkyl);

$R_{102}$ is hydrogen or $C_1$–$C_{18}$alkyl or $R_{101}$ and $R_{102}$ together with the nitrogen atom form a 5-membered ring which may have an unsaturated bond or be fused to a benzene ring;

$R_{103}$ is hydrogen or $C_1$–$C_{18}$alky; or

A and A' together are a group

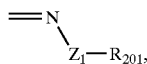

wherein $Z_1$ is O or $NR_{202}$, or when $R_{201}$ represents alkyl or aryl, $Z_1$ is additionally a direct bond;

$R_{202}$ is H, $C_1$–$C_{18}$alkyl or phenyl;

$R_{201}$ is H, straight or branched $C_1$–$C_{18}$alkyl or $C_3$–$C_{18}$alkenyl, which may be unsubstituted or substitued, by one or more OH, $C_1$–$C_8$alkoxy, carboxy, $C_1$–$C_8$alkoxycarbonyl, $C_5C_{12}$cycloalkyl or $C_5$–$C_{12}$cycloalkenyl groups; phenyl, $C_7$–$C_9$phenylalkyl or naphthyl which may be unsubstituted or substituted by one or more $C_1$–$C_8$alkyl, halogen, OH, $C_1$–$C_8$alkoxy, carboxy or $C_1$–$C_8$alkoxycarbonyl groups; or —C(O)—$C_1$–$C_{18}$alkyl, or an acyl moiety of a α,β-unsaturated carboxylic acid having 3 to 9 carbon atoms or of an aromatic carboxylic acid having 7 to 15 carbon atoms; —$SO_3^-Me^+$, —$PO(O^-Me^+)_2$, —$P(O)(OR_2)_2$, —$SO_2R_2$, —CO—NH—$R_2$, —$CONH_2$, $COOR_2$, or $Si(Me)_3$, wherein $Me^+$ is =$H^+$, ammonium or an alkali metal cation; or A is O—$Y_1$ and A' is O—$Y_2$ forming a ketal structure in the 4 position; wherein $Y_1$ and $Y_2$ are independently $C_1$–$C_{12}$alkyl, $C_3$–$C_{12}$alkenyl, $C_3$–$C_{12}$alkinyl, $C_5$–$C_8$cycloalkyl, phenyl, naphthyl or $C_7$–$C_9$phenylalkyl; or $Y_1$ and $Y_2$ together form one of the bivalent groups —$C(R_{301})(R_{302})$—$CH(R_{303})$—, —$CH(R_{301})$—$CH_2$—$C(R_{302})(R_{303})$—, —$CH(R_{302})$—$CH_2$—$C(R_{301})(R_{303})$—, —$CH_2$—$C(R_{301})(R_{302})$—$CH(R_{303})$—, o-phenylene, 1,2-cyclohexylidene, —$CH_2$—CH=CH—$CH_2$— or

wherein $R_{301}$ is hydrogen, $C_1$–$C_{12}$alkyl, COOH, COO—($C_1$–$C_{12}$)alkyl or $CH_2OR_{304}$;

$R_{302}$ and $R_{303}$ are independently hydrogen, methyl, ethyl, COOH or COO—($C_1$–$C_{12}$)alkyl; and $R_{304}$ is hydrogen, $C_1$–$C_{12}$alkyl, benzyl or a monovalent acyl residue derived from an aliphatic, cycloaliphatic or aromatic monocarboxylic acid having up to 18 carbon atoms; and n is a number from 2–20.

14. A process according to claim 13, wherein the scission of the O—C bond is effected by heating and takes place at a temperature of between 50° C. and 160° C.

15. A process for the preparation of a compound of formula Ia, Ib, Ic or Id, which process comprises the steps of a) reacting a compound of formula IIa, IIb, IIc or IId

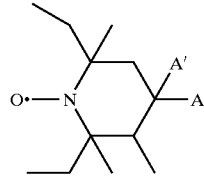
(IIa)

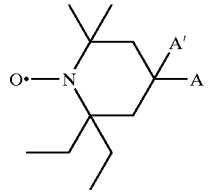
(IIb)

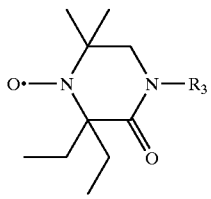
(IIc)

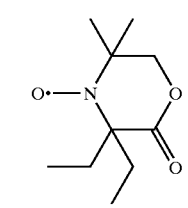
(IId)

with a compound of formula III

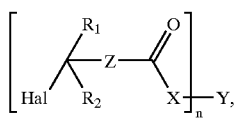 (III)

having a radically transferable group Hal, with a transition metal or transition metal compound in the absence of oxygen;

b) subjecting the reaction mixture to a reduction step; and c) washing the resulting mixture with an aqueous acid solution and isolating the product;

wherein the compounds of formula Ia, Ib, Ic or Id are

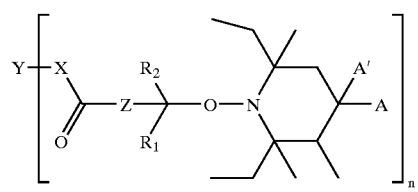 (Ia)

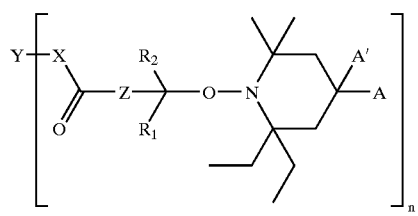 (Ib)

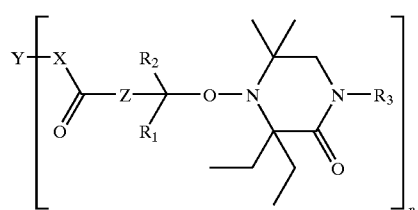 (Ic)

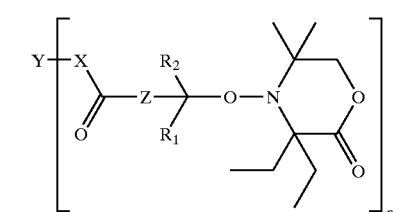 (Id)

wherein $R_1$ and $R_2$ are independently of each other hydrogen, $C_1$–$C_{18}$alkyl or phenyl;

$R_3$ is hydrogen, $C_1$–$C_{18}$alkyl, $C_1$–$C_{18}$alkyl which is substituted by OH, or phenyl which is unsubstituted or substituted by OH, halogen, $C_1$–$C_8$alkoxy or $C_1$–$C_8$alkyl;

X is O, S, $NR_4$ or, if Z is —O—$CH_2$—, X is additionally a direct bond;

$R_4$ is hydrogen or $C_1$–$C_{18}$alkyl;

Z is a direct bond or, if $R_1$ is hydrogen and $R_2$ phenyl, Z is additionally —O—$CH_2$—;

Y is a radical derived from a polyol, a polyamine, a polyaminoalcohol, a polyaminothiol, a polyhydroxythiol, a polyaminohydroxythiol or a polythiol having 2 to 20 —OH, SH and/or —$NR_5$H groups, wherein $R_5$ is hydrogen, $C_1$–$C_{18}$alkyl or phenyl;

or if X is a direct bond and Z is —O—$CH_2$—, Y is a radical derived from a polycarboxylic acid having 2–20 carboxylic functions;

A and A' together are =O; or

A' is hydrogen; and

A is hydrogen, —O—$R_{100}$, wherein $R_{100}$ is hydrogen, $C_1$–$C_{18}$alkyl which is uninterrupted or interrupted by one or more oxygen atoms, $NHR_{100}$, $NR_{100}R_{103}$ or cyanoethyl;

or is a group

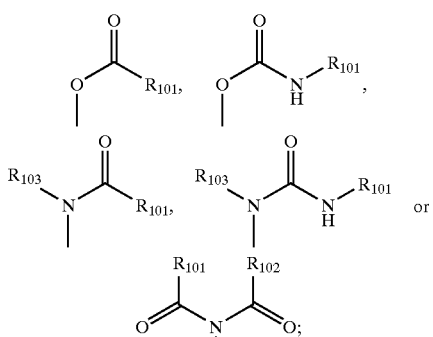

$R_{101}$ is hydrogen, —COOH, —COO($C_1$–$C_4$alkyl), —COO-phenyl, —COObenzyl, $C_1$–$C_8$alkoxy, $C_1$–$C_{18}$alkyl, $C_2$–$C_4$alkenyl, $C_1$–$C_{18}$alkyl or $C_2$–$C_4$alkenyl substituted by OH, —COOH or —COO($C_1$–$C_4$)alkyl, $C_2$–$C_{18}$alkyl which may be interrupted by one or more oxygen atoms, unsubstituted cyclopentyl, cyclohexyl, cyclohexenyl, phenyl or naphthyl; or cyclopentyl, cyclohexyl, cylohexenyl, phenyl or naphthyl which are substituted by $C_1$–$C_4$alkyl, —COOH or —COO—($C_1$–$C_4$alkyl);

$R_{102}$ is hydrogen or $C_1$–$C_{18}$alkyl or $R_{101}$ and $R_{102}$ together with the nitrogen atom form a 5-membered ring which may have an unsaturated bond or be fused to a benzene ring;

$R_{103}$ is hydrogen or $C_1$–$C_{18}$alky; or

A and A' together are a group

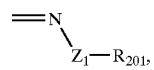

wherein $Z_1$ is O $NR_{202}$, or when $R_{201}$ represents alkyl or aryl, $Z_1$ is additionally a direct bond;

$R_{202}$ is H, $C_1$–$C_{18}$alkyl or phenyl;

$R_{201}$ is H, straight or branched $C_1$–$C_{18}$alkyl or $C_3$–$C_{18}$alkenyl, which may be unsubstituted or substitued, by one or more OH, $C_1$–$C_8$alkoxy, carboxy, $C_1$–$C_8$alkoxycarbonyl, $C_5C_{12}$cycloalkyl or $C_5$–$C_{12}$cycloalkenyl groups; phenyl, $C_7$–$C_9$phenylalkyl or naphthyl which may be unsubstituted or substituted by one or more $C_1$–$C_8$alkyl, halogen, OH, $C_1$–$C_8$alkoxy, carboxy or $C_1$–$C_8$alkoxycarbonyl groups; or —C(O)—$C_1$–$C_{18}$alkyl, or an acyl moiety of a α,β-unsaturated carboxylic acid having 3 to 9 carbon atoms or of an aromatic carboxylic acid having 7 to 15 carbon atoms; —$SO_3^-Me^+$, —$PO(O^-Me^+)_2$, —$P(O)(OR_2)_2$, —$SO_2R_2$, —CO—NH—$R_2$, —$CONH_2$, $COOR_2$, or $Si(Me)_3$, wherein $Me^+$ is =$H^+$, ammonium or an alkali metal cation; or A is O—$Y_1$ and A' is O—$Y_2$ forming a ketal structure in the 4 position; wherein $Y_1$ and $Y_2$ are independently $C_1$–$C_{12}$alkyl, $C_3$–$C_{12}$alkenyl, $C_3$–$C_{12}$alkinyl, $C_5$–$C_8$cycloalkyl, phenyl, naphthyl or $C_7$–$C_9$phenylalkyl; or $Y_1$ and $Y_2$ together form one of the bivalent groups —C($R_{301}$)($R_{302}$)—CH($R_{303}$)—, —CH($R_{301}$)—$CH_2$—C($R_{302}$)($R_{303}$)—, —CH($R_{302}$)—$CH_2$—C($R_{301}$)($R_{303}$)—, —$CH_2$—C($R_{301}$)($R_{302}$)—CH($R_{303}$)—, o-phenylene, 1,2-cyclohexylidene, —$CH_2$—CH=CH—$CH_2$— or

wherein $R_{301}$ is hydrogen, $C_1$–$C_{12}$alkyl, COOH, COO—($C_1$–$C_{12}$)alkyl or $CH_2OR_{304}$;

$R_{302}$ and $R_{303}$ are independently hydrogen, methyl, ethyl, COOH or COO—($C_1$–$C_{12}$)alkyl; and $R_{304}$ is hydrogen, $C_1$–$C_{12}$alkyl, benzyl or a monovalent acyl residue derived from an aliphatic, cycloaliphatic or aromatic monocarboxylic acid having up to 18 carbon atoms; and n is a number from 2–20.

* * * * *